United States Patent
Furutani et al.

(10) Patent No.: US 11,515,594 B2
(45) Date of Patent: Nov. 29, 2022

(54) WATERPROOF DEVICE WITH AIR CELL POWER SOURCE

(71) Applicant: Maxell, Ltd., Kyoto (JP)

(72) Inventors: Takahiro Furutani, Kyoto (JP); Yasuhiro Naka, Kyoto (JP)

(73) Assignee: Maxell, Ltd., Kyoto (JP)

( * ) Notice: Subject to any disclaimer, the term of this patent is extended or adjusted under 35 U.S.C. 154(b) by 299 days.

(21) Appl. No.: 16/633,839

(22) PCT Filed: Aug. 24, 2018

(86) PCT No.: PCT/JP2018/031378
§ 371 (c)(1),
(2) Date: Jan. 24, 2020

(87) PCT Pub. No.: WO2019/065029
PCT Pub. Date: Apr. 4, 2019

(65) Prior Publication Data
US 2020/0373527 A1 Nov. 26, 2020

(30) Foreign Application Priority Data

Sep. 29, 2017 (JP) .............................. JP2017-191440
Jan. 18, 2018 (JP) .............................. JP2018-006258

(51) Int. Cl.
*H01M 50/00* (2021.01)
*H01M 50/14* (2021.01)
(Continued)

(52) U.S. Cl.
CPC ............ *H01M 50/14* (2021.01); *G06F 1/163* (2013.01); *H01M 12/08* (2013.01);
(Continued)

(58) Field of Classification Search
CPC .... H01M 50/14; H01M 50/141; H01M 50/20; H01M 50/202; H01M 12/08; G06F 1/163
See application file for complete search history.

(56) References Cited

U.S. PATENT DOCUMENTS 5,538,807 A * 7/1996 Hagiuda ............... H01M 50/20
   429/100
8,394,134 B2 * 3/2013 Hidaka .................. A61F 7/034
   607/108

(Continued)

FOREIGN PATENT DOCUMENTS

CN     1139363 A  *  1/1997
CN   106900151 A  *  6/2017  ............. A45C 11/00
(Continued)

OTHER PUBLICATIONS

Japanese Office Action for Japanese Application No. 2018-514148, dated Oct. 19, 2021, with English translation.
(Continued)

*Primary Examiner* — Naum Levin
(74) *Attorney, Agent, or Firm* — Birch, Stewart, Kolasch & Birch, LLP

(57) ABSTRACT

Provided is a waterproof device that is impervious to water and can also use an air cell as a power source. The waterproof device of the present disclosure is worn on the body and includes a circuit unit, a power source, and an exterior package that protects the circuit unit and the power source. At least a part of the exterior package is composed of a water-repellent air-permeable sheet. The water-repellent air-permeable sheet has a water pressure resistance of 12 kPa or more.

11 Claims, 5 Drawing Sheets

(51) Int. Cl.
*H01M 12/08* (2006.01)
*H01M 50/20* (2021.01)
*H01M 50/202* (2021.01)
*G06F 1/16* (2006.01)
*H01M 50/141* (2021.01)

(52) U.S. Cl.
CPC ......... *H01M 50/141* (2021.01); *H01M 50/20* (2021.01); *H01M 50/202* (2021.01)

(56) References Cited

U.S. PATENT DOCUMENTS

| | | | |
|---|---|---|---|
| 10,184,586 B2* | 1/2019 | de Jong | H05K 5/0213 |
| 10,199,851 B2* | 2/2019 | Hiroki | H02J 7/342 |
| 10,466,047 B2* | 11/2019 | Ehman | G01L 19/0038 |
| 10,664,020 B2* | 5/2020 | Yoshitani | G06F 3/0412 |
| 10,755,869 B2* | 8/2020 | Kawata | H01G 11/78 |
| 2005/0280531 A1 | 12/2005 | Fadem et al. | |
| 2007/0077485 A1 | 4/2007 | Takamura et al. | |
| 2009/0234410 A1 | 9/2009 | Libbus et al. | |
| 2010/0191078 A1 | 7/2010 | Yodfat et al. | |
| 2012/0208096 A1 | 8/2012 | Kuboki et al. | |
| 2014/0121557 A1 | 5/2014 | Gannon et al. | |
| 2014/0275932 A1 | 9/2014 | Zadig | |
| 2016/0106914 A1 | 4/2016 | Yodfat et al. | |
| 2016/0313769 A1* | 10/2016 | Yoshitani | G06F 1/1694 |
| 2016/0360991 A1 | 12/2016 | Kubota et al. | |

FOREIGN PATENT DOCUMENTS

| | | | | |
|---|---|---|---|---|
| CN | 108463163 A * | 8/2018 | ........... | A61N 1/0551 |
| EP | 2914015 B1 * | 7/2019 | ........... | H04B 1/3888 |
| ES | 2652087 T3 * | 1/2018 | ........ | H01M 10/0413 |
| JP | 04346498 A * | 12/1992 | .......... | H01M 2/1022 |
| JP | 8-173775 A | 7/1996 | | |
| JP | 2008533663 A * | 8/2008 | ........ | H01M 50/1385 |
| JP | 2010-62073 A | 3/2010 | | |
| JP | 2010-534084 A | 11/2010 | | |
| JP | 2012-11326 A | 1/2012 | | |
| JP | 2013-537686 A | 10/2013 | | |
| JP | 5405500 B2 | 2/2014 | | |
| JP | 2014514032 A * | 6/2014 | | |
| JP | 2016-505808 A | 2/2016 | | |
| JP | 2016-515022 A | 5/2016 | | |
| JP | 2017-370 A | 1/2017 | | |
| JP | 2017032975 A * | 2/2017 | ............. | G02F 1/133 |
| JP | 2017101793 A * | 6/2017 | | |
| JP | 2017-143053 A | 8/2017 | | |
| JP | 2017-152086 A | 8/2017 | | |
| JP | 6186097 B1 | 8/2017 | | |
| JP | 2021012378 A * | 2/2021 | ............. | G02F 1/133 |
| KR | 20130047840 A * | 5/2013 | | |
| WO | WO 2005/119830 A1 | 12/2005 | | |
| WO | WO 2008/005016 A1 | 1/2008 | | |
| WO | WO 2009/036316 A1 | 3/2009 | | |
| WO | WO 2011/161822 A1 | 12/2011 | | |
| WO | WO 2012/012558 A2 | 1/2012 | | |
| WO | WO-2013065945 A1 * | 5/2013 | .......... | H01M 10/613 |
| WO | WO-2014107734 A2 * | 7/2014 | ............. | G06F 1/163 |
| WO | WO-2017149526 A2 * | 9/2017 | ........... | G01B 11/026 |

OTHER PUBLICATIONS

Extended European Search Report, dated May 14, 2021, for European Application No. 18861170.1.
International Searching Authority issued in PCT/JP2018/031378 (PCT/ISA/210), dated Oct. 16, 2018.
Japanese Office Action for Japanese Application No. 2019-514148, dated Apr. 26, 2022, with English translation.

* cited by examiner

WATERPROOF DEVICE WITH AIR CELL POWER SOURCE

TECHNICAL FIELD

The present disclosure relates to a waterproof device that is impervious to water and can also use an air cell as a power source.

BACKGROUND ART

In recent years, small measuring devices that are attached to the skin of subjects to measure biological information, including body temperature, respiratory rate, blood pressure, and heart rate, have been increasingly developed. These measuring devices can be used for, e.g., health care, condition monitoring, and treatment of the subjects.

Known examples of the measuring devices are wearable patches (see, e.g., Patent Documents 1 to 3). Such a wearable patch includes a sensor for measuring necessary information, a communication means for transmitting the measured information to another device, and a cell as a power source. The wearable patch can be attached to the human body with an adhesive layer or the like.

In the medical field, the wearable patch is required to be disposable so that it can be disposed of directly after the measurement. Moreover, it is desirable that the cell used in the wearable patch also has a small environmental impact.

Patent Document 3 proposes a medical patch that meets these requirements. The medical patch has a laminated structure including a flexible sheet-type cell, a flexible circuit, an adhesive layer, and a release liner. The flexible sheet-type cell is formed by a printing process, is disposable, and has a small environmental impact. The flexible circuit includes, e.g., a temperature sensor and a communication circuit. The adhesive layer allows the medical patch to stick to the skin.

PRIOR ART DOCUMENTS

Patent Documents

Patent Document 1: JP 2016-515022 A
Patent Document 2: JP 2017-370 A
Patent Document 3: JP 2016-505808 A

DISCLOSURE OF INVENTION

Problem to be Solved by the Invention

A wearable medical device such as a medical patch may get wet with water or may be put in water during use, e.g., when the user wearing the device is taking a bath. With these cases in mind, the wearable patch can be waterproofed by hermetically sealing a device portion (e.g., the sensor, the circuit such as communication means, and the power source) with an exterior material of the wearable patch. However, the wearable patch having this configuration cannot use an air cell that requires air (oxygen) for the reaction of a positive electrode, although it can use an alkaline cell or a lithium cell as a power source. The air cell is promising as a power source because it can be designed for long-term use of the device. If the power source is enclosed in the exterior material of the wearable patch, air cannot be taken into the positive electrode, so that the air cell cannot be operated. Thus, this configuration may limit the type of cells that can be used.

In view of the above situation, it is an object of the present disclosure to provide a waterproof device that is impervious to water and can also use an air cell as a power source.

Means for Solving Problem

A waterproof device disclosed in the present application to solve the above problem is worn on the body and includes a circuit unit, a power source, and an exterior package that protects the circuit unit and the power source. At least a part of the exterior package is composed of a water-repellent air-permeable sheet. The water-repellent air-permeable sheet has a water pressure resistance of 12 kPa or more.

Effects of the Invention

The waterproof device of the present disclosure is able to continue the operation in an environment where the device gets wet with water or is put in water, even if an air cell is used as a power source.

DESCRIPTION OF THE INVENTION

Figure 1:
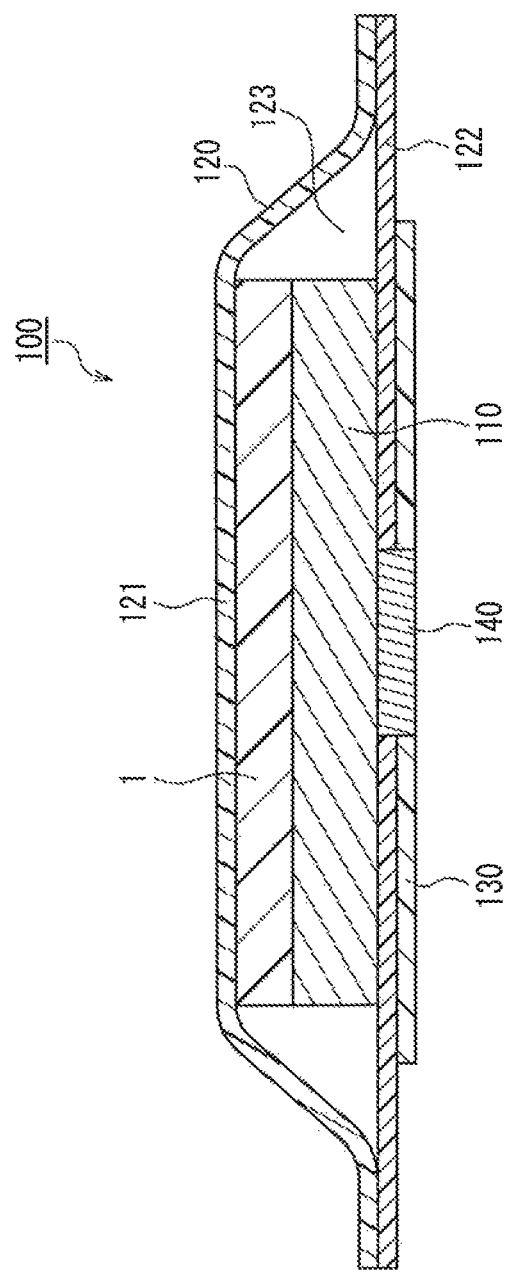
FIG. 1 is a cross-sectional view schematically illustrating an example of a waterproof device of Embodiment 1.

A waterproof device of the present disclosure can be worn on the body and includes a circuit unit, a power source, and an exterior package that protects the circuit unit and the power source. At least a part of the exterior package is composed of an air permeable sheet so that air or water vapor can pass through the exterior package. Thus, when an air cell is used as a power source, air (oxygen) can be supplied to the positive electrode of the air cell.

On the other hand, the air permeable sheet of the exterior package needs to have water repellency to prevent water from adhering to the circuit unit and the power source no matter how the waterproof device gets wet with water or is put in water. That is, at least a part of the exterior package for protecting the circuit unit and the power source should be composed of a water-repellent air-permeable sheet. This configuration can protect the circuit unit and the power source from water droplets while the waterproof device is worn on the body. Therefore, when an air cell is used as the power source, the above configuration can prevent water from entering air holes formed in a package of the air cell and inhibiting the reaction of the positive electrode. Moreover, water vapor released from the body can be diffused through the water-repellent air-permeable sheet to the outside. Thus, it may be possible to reduce the discomfort caused by stuffiness in the portion of the waterproof device that is in contact with the body.

The water pressure resistance of the water-repellent air-permeable sheet may be 12 kPa or more, and preferably 15 kPa or more in order to make the waterproof device sufficiently impervious to water. This can fully prevent water from penetrating the water-repellent air-permeable sheet and can ensure the necessary waterproofness, even if the body of the wearer of the waterproof device is wet or subjected to a certain level of water pressure when it is under water, e.g., when the wearer is taking a bath in daily life.

The upper limit of the water pressure resistance of the water-repellent air-permeable sheet is not particularly limited and is usually about 800 kPa.

In this specification, the water pressure resistance of the water-repellent air-permeable sheet is determined by the B method (high water pressure method) in accordance with JIS L 1092.

The device of the present disclosure may include a functional element that comes into contact with the skin, a drive circuit unit that operates the functional element, a sheet-type cell as the power source in which a power generation element, including a positive electrode and a negative electrode, is sealed between two sheet-type outer case members, and an adhesive layer that is formed on the inner surface. It is preferable that one of the sheet-type outer case members that is on the outer side of the sheet-type cell constitutes a part of the exterior package that is a shell member provided on the outer surface side of the entire device. Thus, the waterproof device can have a simple configuration with a reduced number of members constituting the waterproof device, as compared to a configuration in which the cell (operating power source) and the drive circuit unit are placed inside the shell member, i.e., the exterior package that forms a shell of the waterproof device. Consequently, the waterproof device of the present disclosure can be compact and lightweight while using the sheet-type cell with necessary capacity to perform the function, and is not likely to give an uncomfortable feeling to the wearer.

In this specification, when the waterproof device is worn on the human body, the surface of the device exposed to the outside is referred to as an outer surface, and the surface of the device facing the skin of the human body is referred to as an inner surface.

In the waterproof device of the present disclosure, it is preferable that the drive circuit unit and the sheet-type cell are stacked. This configuration can increase the area of the sheet-type cell and expand the cell capacity.

Moreover, it is preferable that the sheet-type cell is an air cell, and that the water-repellent air-permeable sheet is disposed in a portion of the sheet-type outer case member that is on the outer side of the sheet-type cell and faces the positive electrode. Thus, the waterproof device can have a simple configuration including the sheet-type cell that uses oxygen in the air as a positive electrode active material and is able to increase the cell capacity per volume.

Hereinafter, the waterproof device of the present disclosure will be described with reference to the drawings.

The drawings that illustrate the structure of the waterproof device of this embodiment are intended to clarify the shapes of the members constituting the waterproof device and the correlation between their positions. Thus, the size of each member in the drawings does not necessarily reflect the actual size.

Embodiment 1

FIG. 1 is a cross-sectional view schematically illustrating an example of a waterproof device of Embodiment 1 of the present disclosure.

As shown in FIG. 1, a waterproof device 100 includes a base 122, a drive circuit unit (circuit unit) 110 that is formed on the base 122, a cell (power source) 1 that is placed on the drive circuit unit 110, and an exterior package (shell member) 120 that is provided on the outer surface side (i.e., the opposite side of the body when the waterproof device is worn on the body) and protects the drive circuit unit 110 and the cell 1. For the purpose of brevity, FIG. 1 does not illustrate the details of the cell 1 and the drive circuit unit 110.

The cell 1 and the drive circuit unit 110 (which is the main body of the waterproof device) are held in a space 123 defined by the exterior package 120 and the base 122 that is provided on the inner surface side (i.e., the side facing the skin of the human body). The cell 1 is electrically connected to the drive circuit unit 110. The base 122 has an adhesive layer 130 and can be directly attached to the body via the adhesive layer 130. Moreover, the circuit unit has a functional element 140 that detects biological information such as body temperature of the wearer of the waterproof device 100 and gives some treatment to the wearer. The whole of the exterior package 120 is composed of a water-repellent air-permeable sheet 121.

The peripheral portion of the exterior package 120 is bonded to the base 122 by an adhesive or thermal fusion so that the exterior package 120 is integrated with the base 122.

The material of the base 122 is not particularly limited and may be, e.g., polyolefins such as polyethylene (PE) and polypropylene (PP), polyester, polyurethane, pulp, rayon, or nylon. The base 122 preferably has a thickness of, e.g., about 20 to 600 μm to improve the water permeation while maintaining the strength.

The base 122 may also be a water-repellent air-permeable sheet, as will be described later, or may be made of the same material as that of the exterior package 120.

The air permeability of the water-repellent air-permeable sheet is preferably 60000 sec/100 ml or less, and more preferably 6000 sec/100 ml or less. If the air permeability of the water-repellent air-permeable sheet is too small, the sheet may have low strength as an exterior material and cannot ensure the required water pressure resistance. Therefore, the air permeability of the water-repellent air-permeable sheet is preferably 20 sec/100 ml or more.

In this specification, the air permeability of the water-repellent air-permeable sheet is determined by the Gurley method in accordance with JIS P 8117.

The water-repellent air-permeable sheet may form a part or the whole of the exterior package of the waterproof device. As the water-repellent air-permeable sheet becomes thicker to some extent, the waterproof device tends to give a better feeling of use when it is worn directly on the body. Thus, the thickness of the water-repellent air-permeable sheet is preferably 0.01 mm or more, and more preferably 0.05 mm or more. However, if the water-repellent air-permeable sheet is too thick, the usability of the waterproof device may be reduced due to, e.g., an excessive increase in the thickness of the waterproof device. Therefore, the thickness of the water-repellent air-permeable sheet is preferably 3 mm or less, more preferably 1 mm or less, and particularly preferably 0.5 mm or less.

The water-repellent air-permeable sheet may be formed of only a porous sheet with water repellency or a laminated sheet of, e.g., a porous sheet with water repellency and a support sheet for maintaining the strength.

When the water-repellent air-permeable sheet is formed of only the porous sheet with water repellency or the laminated sheet of the porous sheet with water repellency and the support sheet, the porous sheet with water repellency may be made of, e.g., PE, PP, or polytetrafluoroethylene (PTFE) (such as a sheet in which a large number of pores are formed by a drawing process or the like, similarly to the porous sheet used as a separator of a cell). The porous sheet with water repellency may have a single-layer structure or a multi-layer structure including, e.g., two or more sheets of different resins.

When the water-repellent air-permeable sheet is the laminated sheet having the support sheet, the support sheet may be, e.g., a nonwoven fabric sheet or a rubber sheet.

The nonwoven fabric sheet may be made of e.g., PE, PP, polyethylene terephthalate (PET), or nylon. The nonwoven fabric sheet may have a single-layer structure or a multi-layer structure including, e.g., two or more nonwoven fabric sheets of different resins.

The rubber sheet may be, e.g., a urethane rubber sheet or a silicone rubber sheet. Although these rubber sheets may be porous, since the rubber of the rubber sheets is permeable to air, the rubber sheets may not need any pores.

The porosity of the porous sheet with water repellency is not particularly limited as long as the water-repellent air-permeable sheet meets the above water pressure resistance.

When the water-repellent air-permeable sheet is the laminated sheet of the porous sheet with water repellency and the support sheet, the thicknesses of the porous sheet and the support sheet are not particularly limited as long as the water-repellent air-permeable sheet meets the above preferred thickness and the above water pressure resistance.

Examples of the water-repellent air-permeable sheet may include commercially available products such as "BREATHRON (trade name)" manufactured by Nitoms, Inc., "Tyvek (trade name)" manufactured by DuPont, "POREFLON (trade name)" manufactured by Sumitomo Electric Industries Ltd., "GORE-TEX (trade name)" manufactured by W. L. Gore & Associates, Inc., and "TEMISH (trade name)" manufactured by Nitto Denko Corporation.

The whole of the exterior package of the waterproof device may be composed of the water-repellent air-permeable sheet. Moreover, only a part of the exterior package may be composed of the water-repellent air-permeable sheet if it is sufficiently permeable to air and water vapor. The greater the ratio of the area of the water-repellent air-permeable sheet to the area of the entire exterior package, the larger the amount of air and water vapor passing through the exterior package per unit time. This can make the waterproof device less stuffy when it is worn by the wearer.

When the waterproof device uses an air cell as the power source, at least a certain amount of air needs to pass through the exterior package per unit time to improve the operating condition of the air cell.

Therefore, the ratio of the area of the water-repellent air-permeable sheet to the area of the entire exterior package is preferably 10% or more, and more preferably 30% or more.

In order to take air efficiently into the positive electrode of the air cell, it is preferable that the air cell is placed so that air holes formed in a package of the air cell face the water-repellent air-permeable sheet.

When only a part of the exterior package of the waterproof device is composed of the water-repellent air-permeable sheet, a portion of the exterior package other than the water-repellent air-permeable sheet may be composed of a resin sheet without pores (made of, e.g., PE, PP polyethylene terephthalate, or nylon).

The cell used as the power source of the waterproof device may include, e.g., a positive electrode, a negative electrode, a separator, and an electrolyte that are contained in a package. The type of the cell is not particularly limited, and any cell suitable for small electronic devices may be used.

Figure 2:
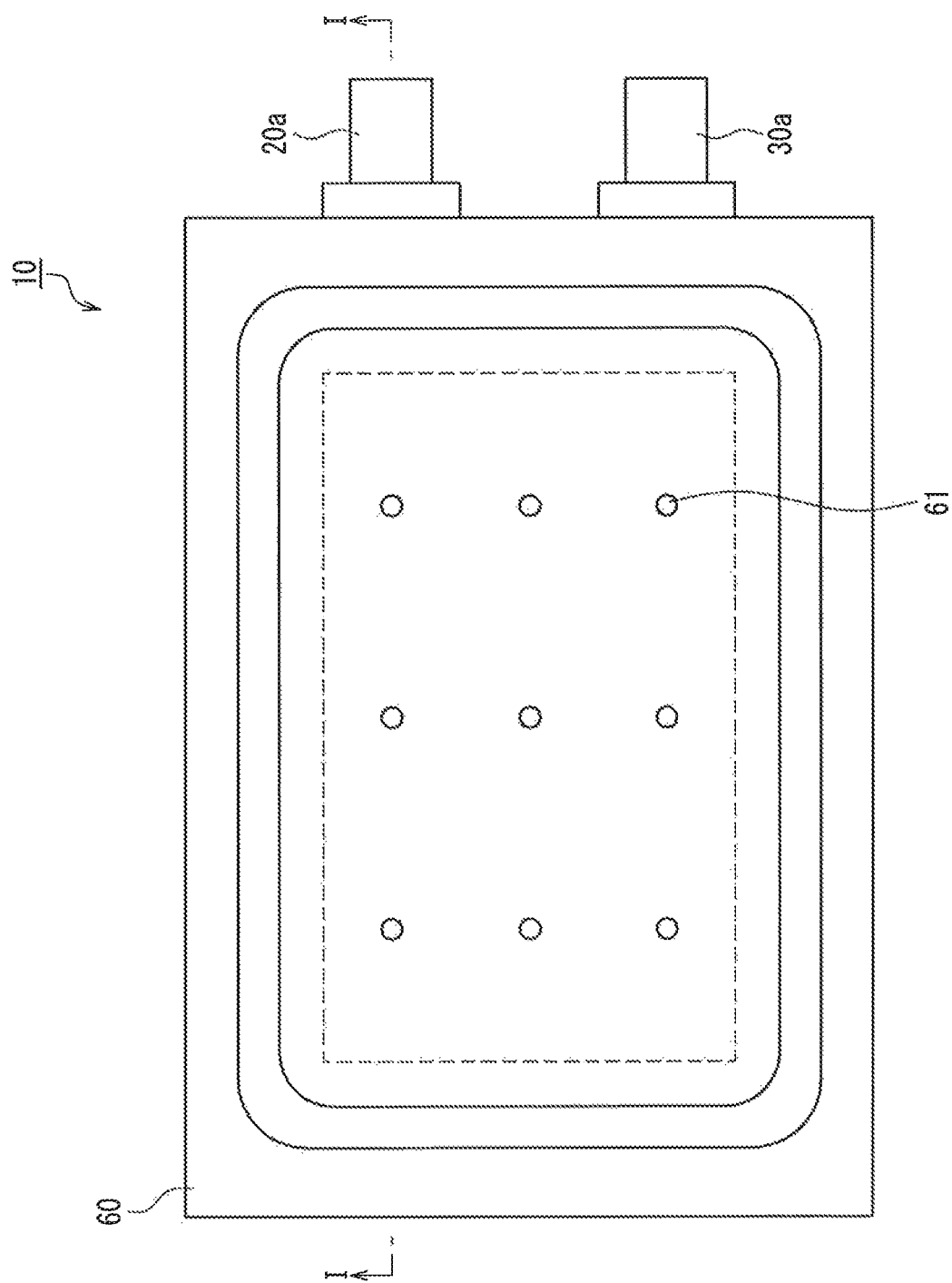
FIG. 2 is a plan view schematically illustrating an example of an air cell that can be used in the waterproof device of Embodiment 1.
Figure 3:
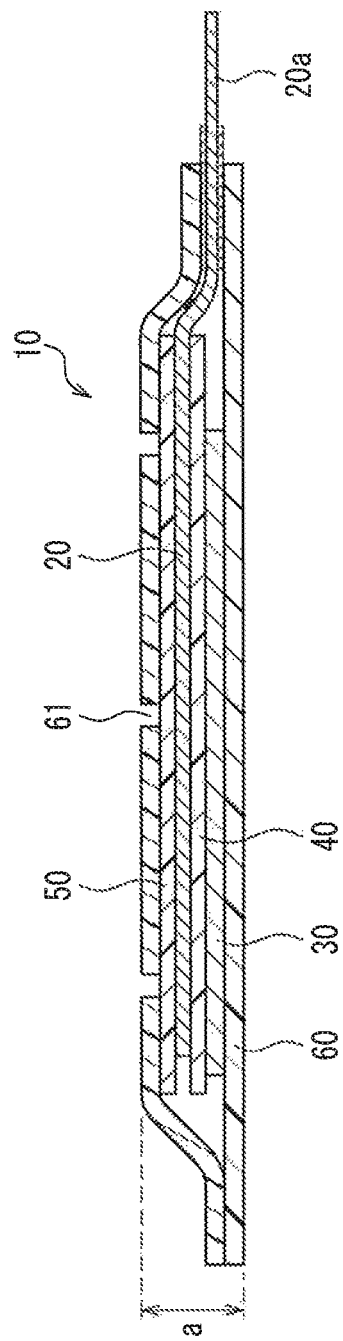
FIG. 3 is a cross-sectional view schematically illustrating an example of an air cell that can be used in the waterproof device of Embodiment 1.

FIGS. 2 and 3 schematically illustrate an example of an air cell that can be used in the waterproof device of this embodiment. FIG. 2 is a plan view of the air cell. FIG. 3 is a cross-sectional view of the air cell. FIG. 3 shows a cross section taken along the line I-I in FIG. 2.

An air cell 10 shown in FIGS. 2 and 3 is an example of a sheet-type air cell that includes a positive electrode 20, a negative electrode 30, a separator 40, and an electrolyte (not shown) that are contained in a sheet-type package (sheet-type outer case) 60. In the air cell 10, the positive electrode 20 is connected to a positive electrode external terminal 20$a$ via a lead and, although not shown, the negative electrode 30 is also connected to a negative electrode external terminal 30$a$ via a lead.

The positive electrode of the air cell may have, e.g., a catalyst layer and a current collector, as will be described later. For the purpose of brevity, the individual layers of the positive electrode 20 are not distinguished from each other in FIG. 3. In FIG. 2, the dotted line represents the size of the catalyst layer of the positive electrode 20 contained in the sheet-type package 60.

The sheet-type package 60 has a plurality of air holes 61 in the side where the positive electrode 20 is provided so as to take air into the positive electrode. Moreover, a water repellent membrane 50 is located on the inner side to prevent leakage of the electrolyte through the air holes 61.

The positive electrode (air electrode) of the air cell has a catalyst layer. For example, the positive electrode with a laminated structure of the catalyst layer and the current collector may be used.

The catalyst layer may contain, e.g., a catalyst and a binder.

Examples of the catalyst of the catalyst layer include the following: silver; platinum metals or alloys thereof, transition metals; platinum/metal oxides such as Pt/IrO$_2$; perovskite oxides such as La$_{1-x}$Ca$_x$CoO$_3$; carbides such as WC; nitrides such as Mn$_4$N; manganese oxides such as manganese dioxide; and carbon (including, e.g., graphite, carbon black (acetylene black, Ketjenblack, channel black, furnace black, lamp black, thermal black, etc.), charcoal, and activated carbon). These catalysts may be used alone or in combinations of two or more.

The heavy metal content in the catalyst layer, except for the components of an electrolyte solution, is preferably 1% by mass or less. When the positive electrode has the catalyst layer with a low heavy metal content, the environmental impact can be reduced even if the cell is disposed of without any special treatment.

The heavy metal content in the catalyst layer can be measured by X-ray fluorescence analysis. For example, the measurement can be performed using "ZSX100e" manufactured by Rigaku Corporation under the following conditions: excitation source, Rh 50 kV and analysis area, $\varphi$ 10 mm.

Thus, catalysts containing no heavy metal are recommended as the catalyst of the catalyst layer, and the above carbon is more preferred.

In terms of further improving the reactivity of the positive electrode, the specific surface area of the carbon that is used as the catalyst is preferably 200 m$^2$/g or more, more preferably 300 m$^2$/g or more, and further preferably 500 m$^2$/g or more. The specific surface area of the carbon is determined by a BET method in accordance with JIS K 6217. For example, the specific surface area of the carbon can be measured with a specific surface area measuring device ("Macsorb HM model-1201" manufactured by Mountech Co., Ltd.) based on a nitrogen adsorption method. The upper limit of the specific surface area of the carbon is usually about 2000 m²/g.

The content of the catalyst in the catalyst layer is preferably 20 to 70% by mass.

Examples of the binder of the catalyst layer include fluorocarbon resin binders such as polyvinylidene fluoride (PVDF), PTFE, copolymers of vinylidene fluoride, and copolymers of tetrafluoroethylene (including, e.g., a vinylidene fluoride-hexafluoropropylene copolymer (PVDF-HFP), a vinylidene fluoride-chlorotrifluoroethylene copolymer (PVDF-CTFE), a vinylidene fluoride-tetrafluoroethylene copolymer (PVDF-TFE), and a vinylidene fluoride-hexafluoropropylene-tetrafluoroethylene copolymer (PVDF-HFP-TFE)). Among them, polymers of tetrafluoroethylene (PTFE) or copolymers of tetrafluoroethylene are preferred, and PTFE is more preferred. The content of the binder in the catalyst layer is preferably 3 to 50% by mass.

The positive electrode can be produced by, e.g., mixing the above catalyst, binder, or the like with water, rolling the mixture between rotating rolls, and bringing the rolled material into close contact with the current collector. There may be another way of producing the positive electrode. First, a composition (slurry, paste, etc.) for forming a catalyst layer is prepared by dispersing the above catalyst and optionally the binder or the like in water or an organic solvent. Then, the composition is applied to the surface of the current collector and dried, which is further subjected to pressing (e.g., calendering) as needed.

The current collector of the positive electrode may be, e.g., a mesh, foil, expanded metal, or punched metal made of metals such as titanium, nickel, stainless steel, and copper or may be, e.g., a mesh or sheet made of carbon. The thickness of the current collector of the positive electrode is preferably 10 to 300 μm.

Moreover, when the air cell has the sheet-type package made of a resin film or a laminated material of a resin film and a metal film, the resin film or a part of the laminated material may also be used as the current collector of the positive electrode. In such a case, e.g., the current collector can be provided by applying a carbon paste to the surface of the resin film or the laminated material that is to be the inner surface of the sheet-type package. Alternatively, the metal layer of the laminated material can also serve as the current collector. Then, a positive electrode mixture layer or the catalyst layer can be formed on the surface of the current collector in the same manner as described above, thus producing the positive electrode. The thickness of the carbon paste layer is preferably 30 to 300 μm.

The negative electrode of the air cell may be made of, e.g., metal particles or metal foil containing a metal material. Examples of the metal material include the following: a zinc-based material (which collectively refers to both a zinc material and a zinc alloy material); a magnesium-based material (which collectively refers to both a magnesium material and a magnesium alloy material); and an aluminum-based material (which collectively refers to both an aluminum material and an aluminum alloy material). In this negative electrode, metals such as zinc, magnesium, and aluminum act as an active material.

The alloy constituents of the zinc alloy material may be, e.g., indium (the content is, e.g., 0.005 to 0.05% by mass), bismuth (the content is, e.g., 0.005 to 0.05% by mass), and aluminum (the content is, e.g., 0.001 to 0.15% by mass).

The alloy constituents of the magnesium alloy material may be, e.g., calcium (the content is, e.g., 1 to 3% by mass), manganese (the content is, e.g., 0.1 to 0.5% by mass), zinc (the content is, e.g., 0.4 to 1% by mass), and aluminum (the content is, e.g., 8 to 10% by mass).

The alloy constituents of the aluminum alloy material may be, e.g., zinc (the content is, e.g., 0.5 to 10% by mass), tin (the content is, e.g., 0.04 to 1.0% by mass), gallium (the content is, e.g., 0.003 to 1.0% by mass), silicon (the content is, e.g., 0.05% by mass or less), iron (the content is, e.g., 0.1% by mass or less), magnesium (the content is, e.g., 0.1 to 2.0% by mass), and manganese (the content is, e.g., 0.01 to 0.5% by mass).

The negative electrode may contain only one type of metal particles or two or more types of metal particles.

In view of a reduction in the environmental impact of the cell for disposal, it is preferable that the metal material used for the negative electrode contains the smallest possible amount of mercury, cadmium, lead, and chromium. Specifically, it is more preferable that the mercury content is 0.1% by mass or less, the cadmium content is 0.01% by mass or less, the lead content is 0.1% by mass or less, and the chromium content is 0.1% by mass or less.

The particle size of the zinc-based material may be defined as follows. For example, the proportion of the particles with a particle diameter of 75 μm or less is preferably 50% by mass or less, and more preferably 30% by mass or less of all particles. Moreover, the proportion of the particles with a particle diameter of 100 to 200 μm may be 50% by mass or more, and more preferably 90% by mass or more of all particles.

The particle size of the magnesium-based material and the aluminum-based material may be defined as follows. For example, the proportion of the particles with a particle diameter of 30 μm or less is preferably 50% by mass or less, and more preferably 30% by mass or less of all particles. Moreover, the proportion of the particles with a particle diameter of 50 to 200 μm may be 50% by mass or more, and more preferably 90% by mass or more of all particles.

In this specification, the particle size of the metal particles means a particle diameter ($D_{50}$) at a cumulative frequency of 50% in the volume-based distribution, which is measured with a laser scattering particle size distribution analyzer (e.g., "LA-920" manufactured by HORIBA, Ltd.) by dispersing the particles in a medium that does not dissolve those particles.

When the negative electrode contains the metal particles, e.g., a thickening agent (such as sodium polyacrylate or CMC (particularly, CMC having the degree of etherification, as will be described below, which is suitable for the thickening agent for the electrolyte)) and a binder may be added to the negative electrode as needed. This may be mixed with an electrolyte solution to form a negative electrode agent (such as a gel-like negative electrode). The amount of the thickening agent in the negative electrode is preferably, e.g., 0.5 to 1.5% by mass. The amount of the binder in the negative electrode is preferably 0.5 to 3% by mass.

The electrolyte solution used for the negative electrode containing the metal particles may be the same as that injected into the cell (i.e., the electrolyte solution used as an electrolyte).

The content of the metal particles in the negative electrode is preferably, e.g., 60% by mass or more, and more preferably 65% by mass or more. The content of the metal particles in the negative electrode is also preferably 95% by mass or less, and more preferably 90% by mass or less.

The negative electrode containing the metal particles preferably contains an indium compound. The presence of the indium compound in the negative electrode can more effectively prevent the generation of hydrogen gas due to a corrosion reaction between the metal particles and the electrolyte.

Examples of the indium compound include indium oxide and indium hydroxide.

The amount of the indium compound in the negative electrode is preferably 0.003 to 1 with respect to 100 of the metal particles at a mass ratio.

When the negative electrode is made of metal foil, the thickness is preferably 10 to 500 µm.

The negative electrode may include a current collector as needed. The current collector of the negative electrode may be, e.g., a mesh, foil, expanded metal, or punched metal made of metals such as nickel, copper, and stainless steel or may be, e.g., a sheet or mesh made of carbon. The thickness of the current collector of the negative electrode is preferably 10 to 300 µm.

When the air cell has the sheet-type package, like the positive electrode, the current collector of the negative electrode can be provided by applying a carbon paste to the surface that is to be the inner surface of the sheet-type package. Alternatively, the metal layer of the sheet-type package can also serve as the current collector. The thickness of the carbon paste layer is preferably 50 to 200 µm.

The separator of the air cell may be any separator that is generally used in various cells. Examples of the separator include a porous resin film (such as a microporous film or nonwoven fabric) and a semipermeable membrane typified by a cellophane film. In terms of preventing a short circuit of the air cell and improving the load characteristics, the separator is preferably made of a semipermeable membrane.

When the separator is made of a resin porous film, polyolefins such as PE, PP and an ethylene-propylene copolymer may be used.

The resin separator preferably has a porosity of 30 to 80% and a thickness of 10 to 100 µm.

When the separator is made of a semipermeable membrane such as a cellophane film, it may consist only of the semipermeable membrane. However, the semipermeable membrane can easily be damaged during cell assembly because of its low strength. Therefore, it is also recommended that the separator should be made of a laminated material of the semipermeable membrane and a grafted film of a particular polymer.

The graft polymer of the grafted film is composed of, e.g., (meth)acrylic acid or its derivative that is graft-polymerized onto polyolefin (polyethylene, polypropylene, etc.), which is a backbone polymer. However, any graft polymer in this form may be used and is not limited to the method of graft polymerization of (meth)acrylic acid or its derivative onto polyolefin.

The (meth)acrylic acid or its derivative of the graft polymer is expressed by the following general formula (1). In the general formula (1), $R^1$ represents H or $CH_3$ and $R^2$ represents H or a hydrophilic substituent such as $NH_4$, Na, K, Rb, or Cs.

[Chemical Formula 1]

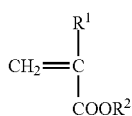

(1)

In the grafted film and the cellophane film, their polymers have the ability to absorb the electrolyte (electrolyte solution) and allow ions to pass through them.

The graft polymer of the grafted film preferably has a graft ratio of 160% or more. The graft ratio is defined by the following formula (2). There is a correlation between the graft ratio of the graft polymer and the electrical resistance of the grafted film. Therefore, when the graft polymer with the above graft ratio is used, the electrical resistance of the grafted film can be controlled in the range of 20 to 120 $m\Omega \cdot in^2$, which are suitable values. The electrical resistance of the grafted film may be determined by an AC voltage drop method (1 kHz). In this method, the film is immersed in a 40% KOH (specific gravity: 1.400±0.005) aqueous solution at 25±1° C. while the ambient temperature is set to 20 to 25° C. Then, the film is taken out after 5 to 15 hours, and the electrical resistance can be measured.

$$\text{Graft ratio (\%)} = 100 \times (A - B)/B \quad (2)$$

In the formula (2), A represents the mass (g) of the graft polymer and B represents the mass (g) of the backbone polymer in the graft polymer. For example, when the graft polymer is formed by graft polymerization of (meth)acrylic acid or its derivative onto polyolefin (backbone polymer), the value "B (the mass of the backbone polymer in the graft polymer)" in the formula (2) can be obtained by previously measuring the mass of the backbone polymer used for this graft polymerization. The graft ratio of the graft polymer may be more than 100% because, in some cases, the monomers (i.e., the (meth)acrylic acid or its derivative) are polymerized with each other, rather than graft-polymerized, so that the graft molecules can have a long chain. The upper limit of the graft ratio of the graft polymer as defined by the formula (2) is preferably 400%. The term "(meth)acrylic acid" collectively refers to both acrylic acid and methacrylic acid.

When the separator consists only of a cellophane film, the thickness of the separator is preferably, e.g., 15 µm or more. The thickness of the separator is also preferably 40 µm or less, and more preferably 30 µm or less.

When the separator is made of a laminated material of a grafted film and a cellophane film, the thickness of the separator, i.e., the total thickness of the grafted film and the cellophane film is preferably, e.g., 30 µm or more, and more preferably 40 µm or more. The thickness of the separator is also preferably 70 µm or less, and more preferably 60 µm or less.

Moreover, when the separator is made of a laminated material of a grafted film and a cellophane film, the thickness of the grafted film is preferably, e.g., 15 µm or more, and more preferably 25 µm or more. The thickness of the grafted film is also preferably 30 µm or less.

The laminated material of the grafted film and the cellophane film used for the separator is commercially available, e.g., from Yuasa Membrane Systems Co., Ltd. under the name of "YG9132", "YG9122", or "YG2152".

The separator may be formed by combining, e.g., the cellophane film or both the cellophane film and the grafted film with a liquid-absorbing layer (i.e., an electrolyte solution holding layer) such as vinylon-rayon mixed paper. In this case, the thickness of the liquid-absorbing layer is preferably 20 to 500 µm.

The electrolyte of the air cell may be, e.g., an aqueous solution containing an electrolyte salt (electrolyte solution). The pH of the aqueous solution used as the electrolyte is preferably 3 or more, and more preferably 5 or more. The pH of the aqueous solution is also preferably less than 12, more preferably 10 or less, and further preferably less than 7. Compared to, e.g., a strong alkaline aqueous solution that has a high pH (of about 14) and is generally used in the air cell, the aqueous solution with the above pH is unlikely to be a problem even if the electrolyte adheres to the human body due to, e.g., damage to the air cell (the waterproof device including the air cell) during use or disposal. Thus, the air cell using the aqueous solution as the electrolyte can have high safety and reduce the environmental impact after disposal.

Examples of the electrolyte salt dissolved in the aqueous solution used as the electrolyte include the following: chlorides such as sodium chloride, potassium chloride, magnesium chloride, calcium chloride, ammonium chloride, and zinc chloride; hydroxides of alkali metals or alkaline-earth metals (e.g., sodium hydroxide, potassium hydroxide, and magnesium hydroxide), acetates (e.g., sodium acetate, potassium acetate, and magnesium acetate), nitrates (e.g., sodium nitrate, potassium nitrate, and magnesium nitrate), sulfates (e.g., sodium sulfate, potassium sulfate, and magnesium sulfate), phosphates (e.g., sodium phosphate, potassium phosphate, and magnesium phosphate), borates (e.g., sodium borate, potassium borate, and magnesium borate), citrates (e.g., sodium citrate, potassium citrate, and magnesium citrate), and glutamates (e.g., sodium glutamate, potassium glutamate, and magnesium glutamate); hydrogencarbonates of alkali metals (e.g., sodium hydrogencarbonate and potassium hydrogencarbonate); percarbonates of alkali metals (e.g., sodium percarbonate and potassium percarbonate); compounds containing halogens such as fluorides; and polycarboxylic acids. The aqueous solution may contain either one or two or more of these electrolyte salts.

As the electrolyte salt, salts of strong acids and weak bases are preferably used. The strong acids may be selected from hydrochloric acid, sulfuric acid, and nitric acid. The weak bases may be typified by ammonia and hydroxides of metallic elements such as aluminum hydroxide and magnesium hydroxide. Moreover, ammonium salts or salts of particular metallic elements are also preferred. Specifically, salts of at least one type of ions selected from $Cl^-$, $SO_4^{2-}$, $HSO_4^-$, and $NO_3^-$ and at least one type of ions selected from Al ions, Mg ions, Fe ions, and ammonium ions are more preferred. Examples of the salts include the following: ammonium salts such as ammonium sulfate, ammonium hydrogen sulfate (($NH_4$)$HSO_4$), ammonium chloride, and ammonium nitrate; aluminum salts such as aluminum sulfate, aluminum chloride, and aluminum nitrate; magnesium salts such as magnesium sulfate, magnesium chloride, magnesium chloride hydroxide ($MgCl(OH)$), and magnesium nitrate; and iron salts such as iron (II) sulfate, iron (II) ammonium sulfate (($NH_4$)$_2Fe(SO_4)_2$), iron (III) sulfate, iron (II) chloride, and iron (II) nitrate.

The electrolyte, which is the aqueous solution containing the above salts of strong acids and weak bases, has a relatively weak corrosive action on metals or alloys that can be a negative electrode active material, as compared to the electrolyte containing salts of strong acids and strong bases such as sodium chloride. Moreover, the electrolyte containing salts of metallic elements selected from Al, Mg, and Fe or ammonium salts have a relatively high conductivity, as compared to, e.g., an aqueous solution of zinc chloride. Thus, the use of the electrolyte which is the aqueous solution containing the salts of strong acids and weak bases, i.e., the salts of at least one type of ions selected from $Cl^-$, $SO_4^{2-}$, $HSO_4^-$, and $NO_3^-$ and at least one type of ions selected from Al ions, Mg ions, Fe ions, and ammonium ions can further improve the discharge characteristics of the air cell.

The salt of $Cl^-$ ions and $Fe^{3+}$ ions (i.e., iron (III) chloride) has a strong corrosive action on a metal material that can be a negative electrode active material, as compared to salts of other combinations of ions. Therefore, salts other than iron (III) chloride are preferably used. Moreover, ammonium salts are more preferred because they have a lower corrosive action on the metal material.

Among the above salts of strong acids and weak bases, perchlorate may create a risk of combustion or explosion when it is heated or subjected to shock. Therefore, from the viewpoint of environmental impact and safety of disposal, perchlorate should not be contained in the aqueous solution. Even if it is contained, the amount of perchloric acid ions is preferably as small as possible (i.e., preferably less than 100 ppm, and more preferably less than 10 ppm).

Among the above salts of strong acids and weak bases, heavy metal salts (other than iron salts) typified by, e.g., zinc chloride and copper sulfate are often harmful. Therefore, from the viewpoint of environmental impact and safety of disposal, heavy metal salts should not be contained in the aqueous solution. Even if they are contained, the amount of heavy metal ions other than iron ions is preferably as small as possible (i.e., preferably less than 100 ppm, and more preferably less than 10 ppm).

The aqueous solution that can be used as the electrolyte preferably contains a water-soluble high-boiling solvent with a boiling point of 150° C. or more along with water. When the air cell is discharged, the voltage decreases with a decrease in the capacity. In the late stage of discharge, the voltage not only decreases but also tends to vary greatly as the capacity becomes smaller. However, the presence of the water-soluble high-boiling solvent in the aqueous solution can suppress such a voltage variation in the late stage of discharge. Thus, the air cell can have better discharge characteristics.

As shown in FIGS. 2 and 3, the package of the air cell has air holes to introduce air into the positive electrode. There are some cases where water in the electrolyte (electrolyte solution) is vaporized and dissipated through the air holes of the package. Consequently, the composition of the electrolyte can easily be changed, which may result in poor discharge characteristics. However, the presence of the water-soluble high-boiling solvent in the aqueous solution used as the electrolyte can suppress the vaporization of water from the electrolyte and thus can suppress a reduction in discharge characteristics due to the composition change of the electrolyte. Moreover, it is also possible to further improve the storage properties of the air cell.

The upper limit of the boiling point of the water-soluble high-boiling solvent is usually 320° C.

It is desirable that the water-soluble high-boiling solvent has a high surface tension and a high relative dielectric constant in order to more adequately maintain the discharge characteristics of the air cell. When the air cell is discharged, the positive electrode (catalyst layer) needs to be in contact with air. If the surface tension of the water-soluble high-boiling solvent in the electrolyte is low, the surface of the catalyst-containing layer of the positive electrode will be covered with the electrolyte, resulting in a significant increase in the proportion of the surface that is not likely to come into contact with air. This may reduce the discharge characteristics of the cell. However, these problems can be avoided by using the water-soluble high-boiling solvent with a high surface tension.

In general, the relative dielectric constant of an organic solvent is lower than that of water. Therefore, the ionic conduction will be more reduced when the electrolyte is prepared by mixing the organic solvent with water, as compared to using only water. This may degrade the discharge characteristics of the cell. However, these problems can be avoided by using the water-soluble high-boiling solvent with a high relative dielectric constant.

Specifically, the surface tension of the water-soluble high-boiling solvent is preferably 30 mN/m or more. The upper limit of the surface tension of the water-soluble high-boiling solvent is usually 70 mN/m. In this specification, the surface tension of the water-soluble high-boiling solvent may be measured with a Wilhelmy method using a commercially available device (e.g., "CBVP-Z" manufactured by Kyowa Interface Science Co., Ltd).

The relative dielectric constant of the water-soluble high-boiling solvent is preferably 30 or more. The upper limit of the relative dielectric constant of the water-soluble high-boiling solvent is usually 65. In this specification, the relative dielectric constant of the water-soluble high-boiling solvent may be obtained from the dielectric constant that is measured using, e.g., "Precision LCR Meter HP 4284" manufactured by Hewlett Packard.

Specific examples of the water-soluble high-boiling solvent suitable for the electrolyte include the following: polyhydric alcohols such as ethylene glycol (boiling point: 197° C., surface tension: 48 mN/m, relative dielectric constant: 39), propylene glycol (boiling point: 188° C., surface tension: 36 mN/m, relative dielectric constant: 32), and glycerol (boiling point: 290° C., surface tension: 63 mN/m, relative dielectric constant: 43); and polyalkylene glycol (having a molecular weight of preferably 600 or less) such as polyethylene glycol (PEG, e.g., boiling point: 230° C., surface tension: 43 mN/m, relative dielectric constant: 35). The electrolyte may contain either only one or two or more of these water-soluble high-boiling solvents, and more preferably may contain glycerol.

To ensure a good effect of the water-soluble high-boiling solvent when it is used, the content of the water-soluble high-boiling solvent in the aqueous solution is preferably 1% by mass or more, and more preferably 3% by mass or more of the total solvent. However, if the amount of the water-soluble high-boiling solvent in the aqueous solution is too large, the ionic conduction of the aqueous solution becomes too small, so that the cell characteristics may be reduced. Thus, the content of the water-soluble high-boiling solvent in the aqueous solution is preferably 30% by mass or less, and more preferably 20% by mass or less of the total solvent.

The concentration of the electrolyte salt in the aqueous solution may be set so that the conductivity of the aqueous solution can be adjusted, e.g., to about 80 to 700 mS/cm. The concentration of the electrolyte salt is usually 5 to 50% by mass.

It is preferable that an indium compound is dissolved in the solvent (water or a mixed solvent of water and the water-soluble high-boiling solvent) of the aqueous solution used as the electrolyte. When the indium compound is dissolved in the aqueous solution, the generation of hydrogen gas inside the cell can be adequately suppressed.

Examples of the indium compound dissolved in the aqueous solution include indium hydroxide, indium oxide, indium sulfate, indium sulfide, indium nitrate, indium bromide, and indium chloride.

The concentration of the indium compound in the aqueous solution is preferably 0.005% by mass or more, more preferably 0.01% by mass or more, and particularly preferably 0.05% by mass or more. The concentration of the indium compound in the aqueous solution is also preferably 1% by mass or less, more preferably 0.5% by mass or less, and particularly preferably 0.1% by mass or less.

In addition to the above components, the aqueous solution may optionally contain various known additives so as not to impair the effects of the present invention. For example, zinc oxide may be added to the aqueous solution to prevent corrosion (oxidation) of the metal material used for the negative electrode.

The aqueous solution used as the electrolyte may be gelled, and a gel electrolyte is also preferably used as the electrolyte of the air cell. The gel electrolyte may be prepared by mixing a thickening agent and the aqueous solution that contains the electrolyte salt and has a pH of 3 or more and less than 12. The use of the gel electrolyte can also suppress the voltage variation in the late stage of discharge and can further improve the discharge characteristics of the air cell. Moreover, since the vaporization of water from the gel electrolyte is reduced, it is possible to suppress a reduction in discharge characteristics due to the composition change of the electrolyte, and also to further improve the storage properties of the air cell.

The aqueous solution that contains the electrolyte salt and has a pH of 3 or more and less than 12, which is used to prepare the gel electrolyte, may be the same as the aqueous solution that can be used as the electrolyte of the air cell.

The thickening agent used to form the gel electrolyte may be any of various synthetic polymers or natural polymers. Specific examples of the thickening agent include the following: cellulose derivatives such as carboxymethyl cellulose (CMC) and carboxyethyl cellulose (CEO; polyalkylene glycol (having a molecular weight of preferably 10000 or more) such as polyethylene glycol (PEG); polyvinylpyrrolidone; polyvinyl acetate; starch; guar gum; xanthan gum; sodium alginate; hyaluronic acid; and gelatin. The gel electrolyte may be formed by using either only one or two or more of these thickening agents. The molecular weight (average molecular weight) of commercially available polyalkylene glycol such as PEG is generally found on the label. In this specification, the molecular weight of polyalkylene glycol means such a nominal value provided by the manufacturer.

Among the above thickening agents, CMC, xanthan gum, and high molecular weight PEG (with a molecular weight of 100000 or more and preferably 5000000 or less) are more preferred because the effect of thickening the electrolyte (i.e., the electrolyte solution which is the aqueous solution containing the electrolyte salt) is high, and the gel electrolyte with good properties can be more easily prepared.

The CMC is an anionic polymer and is likely to be affected by metal ions or salts when they are present together. Therefore, the effect of thickening the electrolyte may be reduced. However, the CMC with a high degree of etherification is less affected by metal ions or salts and thus can have a better effect of thickening the electrolyte. Specifically, the degree of etherification of the CMC is preferably 0.9 or more, and more preferably 1.0 or more. In this specification, the degree of etherification of the CMC is a value that represents how many carboxymethyl groups are ether-linked to one anhydroglucose unit. The degree of etherification of the CMC is preferably 1.6 or less.

Moreover, when the functional group including a carboxyl group or its salt (—COOH, —COONa, etc.) is present in the molecule of the thickening agent such as CMC, CEC, xanthan gum, or sodium alginate, it is preferable that a polyvalent metal salt serving as a gelation accelerator is added to the electrolyte. In this case, the gelation accelerator acts on the thickening agent so that the electrolyte is more suitably gelled, making it much easier to form the gel electrolyte with good properties.

The polyvalent metal salt that can be used as a gelation accelerator differs according to the type of the thickening agent used. As the polyvalent metal salt, salts of divalent or trivalent metal ions are preferred. Examples of the polyvalent metal salt include the following: alkaline-earth metal salts such as magnesium salts (e.g., magnesium sulfate) and calcium salts (calcium sulfate); aluminum salts such as aluminum nitrate and aluminum sulfate; iron salts such as iron (II) chloride, iron (III) chloride, and iron (III) sulfate; and chromium salts such as chromium nitrate. Among them, aluminum salts and iron salts are more preferred. It is desirable that the aqueous solution having a pH of 3 or more and less than 12 is used to form the gel electrolyte, thereby reducing the environmental impact of the cell. The use of aluminum salts and iron salts as a gelation accelerator can suppress an increase in the environmental impact of the gelation accelerator.

Depending on the combination of the electrolyte salt and the thickening agent, the electrolyte salt itself may function as a gelation accelerator, and it would be impossible to form a uniform gel electrolyte or a gel electrolyte with sufficient ionic conduction. These problems can be prevented in the following manner. For example, the electrolyte salt may be made of only salts of monovalent metal ions or made of salts of polyvalent metal ions in combination with salts of monovalent metal ions. Alternatively, an aqueous solution containing the electrolyte salt and an aqueous solution containing the thickening agent may be prepared separately and then mixed together to form the electrolyte. Moreover, ammonium salts may be preferably used as the electrolyte salt.

In terms of forming the gel electrolyte with good properties and ensuring good ionic conduction, the content of the thickening agent in the electrolyte is preferably 0.1% by mass or more, and more preferably 0.2% by mass or more. The content of the thickening agent in the electrolyte is also preferably 5% by mass or less, and more preferably 3% by mass or less.

When the polyvalent metal salt (gelation accelerator) is added to the electrolyte, in terms of achieving a better effect of the polyvalent metal salt, the content of the polyvalent metal salt is preferably 1 or more, and more preferably 2 or more with respect to 100 of the thickening agent at a mass ratio. Even if the content of the polyvalent metal salt is increased, its effect becomes saturated. Thus, the content of the polyvalent metal salt in the electrolyte is preferably 30 or less, and more preferably 20 or less with respect to 100 of the thickening agent at a mass ratio.

When the electrolyte salt also serves as a gelation accelerator, the content of the gelation accelerator may be set within a suitable concentration range of the electrolyte salt, as described above.

The aqueous solution containing the electrolyte salt may be prepared by dissolving necessary components (including the electrolyte salt, and optionally the water-soluble high-boiling solvent and the indium compound) in water.

The gel electrolyte may be formed in the following manner. For example, first, the aqueous solution that contains the electrolyte salt and has a pH of 3 or more and less than 12 has previously been prepared. Then, the thickening agent and optionally other components (such as the indium compound) are dissolved in the aqueous solution. Moreover, when the water-soluble high-boiling solvent is added, e.g., the water-soluble high-boiling solvent may be mixed with water, and the mixed solvent may be used to prepare the aqueous solution. This aqueous solution may be used to form the gel electrolyte.

The gel electrolyte may contain the thickening agent that has the functional group including a carboxyl group or its salt in the molecule and the polyvalent metal salt that serves as a gelation accelerator. Such a gel electrolyte is preferably formed by mixing (a) a solution in which the thickening agent is further dissolved in the aqueous solution that contains the electrolyte salt and has a pH of 3 or more and less than 12 and (b) an aqueous solution in which the gelation accelerator (polyvalent metal salt) is dissolved. This method can provide a better gel electrolyte than the method of adding the thickening agent and the polyvalent metal salt to the aqueous solution that contains the electrolyte salt and has a pH of 3 or more and less than 12. Further, the solution (a) in which the thickening agent is further dissolved in the aqueous solution that contains the electrolyte salt and has a pH of 3 or more and less than 12 and the aqueous solution (b) in which the gelation accelerator (polyvalent metal salt) is dissolved may be separately put into the outer case of the cell and then mixed together in this outer case. This method is particularly preferred because a better gel electrolyte can be formed more efficiently.

The package of the air cell is not particularly limited, and any package may be used in accordance with the shape and structure of the waterproof device. Examples of the package include a sheet-type package (sheet-type outer case), as shown in FIGS. 2 and 3, and a package made of a metal can that includes a metal outer can, a metal sealing plate, and a resin gasket. The package made of the metal can preferably has a flat shape called coin type or button type.

The sheet-type package may be made of, e.g., a resin film. Examples of the resin film include a nylon film (such as a nylon 66 film) and a polyester film (such as a PET film). The thickness of the resin film is preferably 20 to 100 µm.

The sheet-type package is generally sealed by heat-sealing the edge of the upper resin film and the edge of the lower resin film of the sheet-type package. To further facilitate the heat seal, a heat-sealing resin layer may be formed on the resin film and used to form the sheet-type package. The heat-sealing resin of the heat-sealing resin layer may be, e.g., a modified polyolefin film (such as a modified polyolefin ionomer film) or PP and its copolymer. The thickness of the heat-sealing resin layer is preferably 20 to 100 µm.

Moreover, a metal layer may be formed on the resin film. The metal layer may be, e.g., an aluminum film (including aluminum foil and aluminum alloy foil) or a stainless steel film (including stainless steel foil). The thickness of the metal layer is preferably 10 to 150 µm.

The resin film of the sheet-type package may be, e.g., a laminated film of the heat-sealing resin layer and the metal layer.

The shape of the sheet-type package may be, e.g., a polygon (such as triangle, quadrangle, pentagon, hexagon, heptagon, or octagon), a circle, or an ellipse in a plan view. When the sheet-type package has a polygonal shape in a plan view, the positive electrode external terminal and the negative electrode external terminal may be drawn from the same side or different sides of the sheet-type package to the outside.

The package has air holes in the portion where the positive electrode is to be located so as to take air into the cell. The number of the air holes is not particularly limited and may be set so that a sufficient amount of air can be introduced for successful discharge of the air cell. Moreover, the shape of the air holes is not particularly limited and may be, e.g., a circle, an ellipse, or a polygon (triangle, quadrangle, etc.) in a plan view.

In the air cell, the water repellent membrane is usually placed between the positive electrode and the package, as shown in FIG. 3. The water repellent membrane has not only water repellency, but also air permeability. Specifically, such a water repellent membrane may be made of, e.g., fluororesin such as PTFE or resin such as polyolefin (PE, PP, etc.). The thickness of the water repellent membrane is preferably 50 to 250 μm.

An air diffusion membrane may be provided between the package and the water repellent membrane. The air diffusion membrane is used to supply the air that has been taken inside the package to the positive electrode. The air diffusion membrane may be, e.g., a nonwoven fabric made of resin such as cellulose, polyvinyl alcohol, polypropylene, or nylon. The thickness of the air diffusion membrane is preferably 100 to 250 μm.

The thickness of the air cell (i.e., the length indicated by a in FIG. 3 when the air cell is a sheet-type air cell) is not particularly limited and can be appropriately changed in accordance with the shape and structure of the waterproof device including the air cell. One of the advantages of the sheet-type air cell is that the thickness can be reduced. In view of this, the thickness of the sheet-type air cell is preferably, e.g., 1 mm or less. Moreover, the thickness of the sheet-type air cell is generally preferably 0.2 mm or more to ensure a certain capacity.

On the other hand, when the package is made of the metal can and has a flat shape, the thickness of the package is preferably 3 to 5 mm.

The circuit unit of the waterproof device may be configured in accordance with the intended use of the waterproof device. For example, the waterproof device may be a medical patch that detects biological information such as body temperature of the wearer (subject) or injects a predetermined amount of drug solution into the wearer's body at a predetermined time. In such a case, the circuit unit may include a drive circuit unit and a functional element for detecting predetermined data (e.g., biological information such as body temperature, pulse, and respiratory rate) of the wearer or for giving predetermined treatment (e.g., the injection of a drug solution) to the wearer.

When the waterproof device is used to detect biological information such as body temperature of the wearer, the functional element is preferably a thin member made of a thin plate or a thin film, e.g., a sensor plate for detecting biological information of the wearer. The functional element may be in the form of a metal foil, a resin film on which a conductive member (metal or carbon) is disposed, or the like.

When the waterproof device is used to inject a predetermined amount of drug solution into the wearer's body at a predetermined time, the functional element may include, e.g., a small injection needle, a drug solution container containing the drug solution that is to be injected into the wearer's body, and a pump unit for delivering a predetermined amount of the drug solution from the drug solution container.

As shown in FIG. 1, the functional element is usually exposed from the exterior package, the base, and the adhesive layer so that it can come into direct contact with the skin of the wearer. In some cases, however, the functional element may perform its function even without exposure to the outside, depending on the function of the functional element. For example, if the functional element has the function of being able to detect biological information of the wearer without any direct contact with the skin, the entire functional element can be contained, e.g., in a space defined by the exterior package and the base, thus eliminating a portion of the functional element that is exposed to the outside.

The drive circuit unit may be composed of known thin film electronic circuit components, including, e.g., the following: wiring that is made of a metal thin film such as copper and formed on a film substrate; one or more electronic circuits (thin film chips) that function as a memory, a processor, a transmitting and receiving circuit, etc.; and an antenna element that is made of a metal thin film and used for communication with the outside.

The drive circuit unit may be designed to have the function that is applicable to the intended use of the waterproof device. For example, the waterproof device can measure the body temperature of the wearer in the following manner. The temperature of the sensor plate (functional element) is detected by, e.g., a change in current flowing through the sensor plate, and the measured value of the body temperature is transmitted from the antenna element to a connected external device (e.g., smartphone) in accordance with a control signal from the external device or under the control of a logic circuit included in the drive circuit unit.

When the functional element is a unit for injecting a drug solution into the wearer's body, the drive circuit unit may have the function of being able to inject a predetermined amount of the drug solution into the wearer's body at a predetermined time by using the timer function of the drive circuit unit or in accordance with an operation signal from the external device.

The drive circuit unit and the functional element may be connected, e.g., by bringing a part of the functional element into direct contact with at least a part of the protruding portion of the electronic circuit component of the drive circuit unit or by interposing a conductive means such as wiring between the drive circuit unit and the functional element.

The drive circuit unit and the cell (power source) may be arranged so that, e.g., the cell is stacked on the drive circuit unit, as shown in FIG. 1. With this arrangement, the ratio of the area of the cell to the area of the waterproof device can be close to 100%. Thus, compared to the side-by-side arrangement of the drive circuit unit and the cell, the area of the cell can be made larger if the area of the waterproof device is the same, so that the cell capacity can be increased. On the other hand, if the area of the cell is the same, the area of the waterproof device can be reduced by stacking the cell on the drive circuit unit, compared to the side-by-side arrangement.

When the drive circuit unit and the cell are arranged in layers, the area of the drive circuit unit can be extended to the entire area of the waterproof device. This increases the design margin for the arrangement of various circuit components of the drive circuit unit. For example, the connection wiring may be shortened or thickened to reduce the resistance component, so that the drive circuit unit can be operated with lower power consumption. Moreover, when the drive circuit unit includes an antenna element, the arrangement of the drive circuit unit and the cell in layers can also increase the area of the antenna element and improve the antenna characteristics. Therefore, thinner circuit components can be selected, even though they have a relatively large area, to reduce the thickness of the drive circuit unit, which in turn reduces the thickness of the waterproof device as a whole.

However, when the package includes a metal material such as a laminated film having a metal layer, it is preferable that the arrangement of the cell is adjusted so that the antenna element will not be covered with the package of the cell, in order not to interfere with the communication function of the waterproof device.

On the other hand, if the waterproof device becomes thick, it may be difficult to attach the waterproof device to the skin, or the wearer may feel strongly uncomfortable with the waterproof device. In such a case, the circuit unit and the air cell can be arranged side by side rather than in layers, thereby suppressing an increase in the thickness of the waterproof device as a whole.

As shown in FIG. 1, the waterproof device may optionally include an adhesive layer that allows the waterproof device to stick to the body. The configuration (material, thickness, etc.) of the adhesive layer is not particularly limited. For example, the adhesive layer may be made of the same materials (such as acrylic adhesive, rubber adhesive, silicone adhesive, and hydrogel) used for adhesive layers of known wearable devices (e.g., medical patches) and adhesive plasters. The thickness of the adhesive layer may be, e.g., 30 to 1000 μm so that the waterproof device can be comfortably attached to the body and maintained.

The waterproof device does not need to include the adhesive layer if it can be attached to the body by means other than the adhesive layer (e.g., a rubber band).

The waterproof device of the present disclosure can be used for the same purpose as the wearable device such as a medical patch, which is a conventionally known wearable patch.

Embodiment 2

Next, a waterproof device of the present disclosure according to Embodiment 2 will be described.

The waterproof device of Embodiment 2 is a wearable patch that is worn directly on the body. The waterproof device differs from the waterproof device of Embodiment 1 in the following points: a sheet-type air cell is used as a power source; and a sheet-type outer case member (sheet-type package) that is on the outer side of the sheet-type air cell constitutes a part of the exterior package (shell member) of the entire waterproof device.

Figure 4:
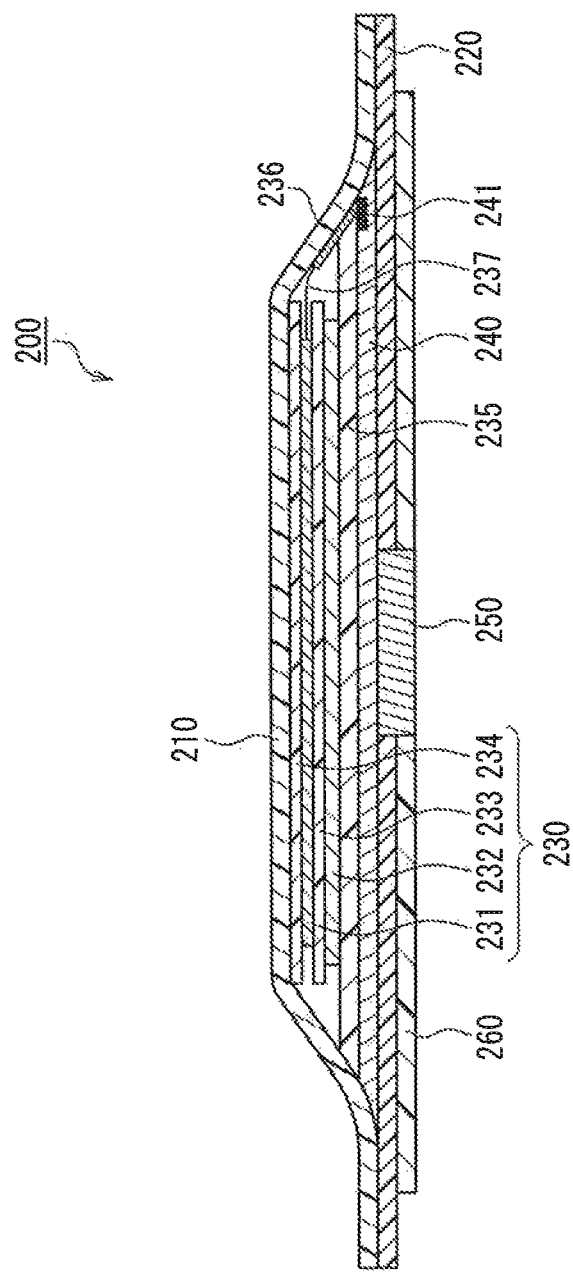
FIG. 4 is a cross-sectional view schematically illustrating an example of a waterproof device of Embodiment 2.

FIG. 4 is a cross-sectional view illustrating the overall configuration of the wearable patch of Embodiment 2.

Figure 5:
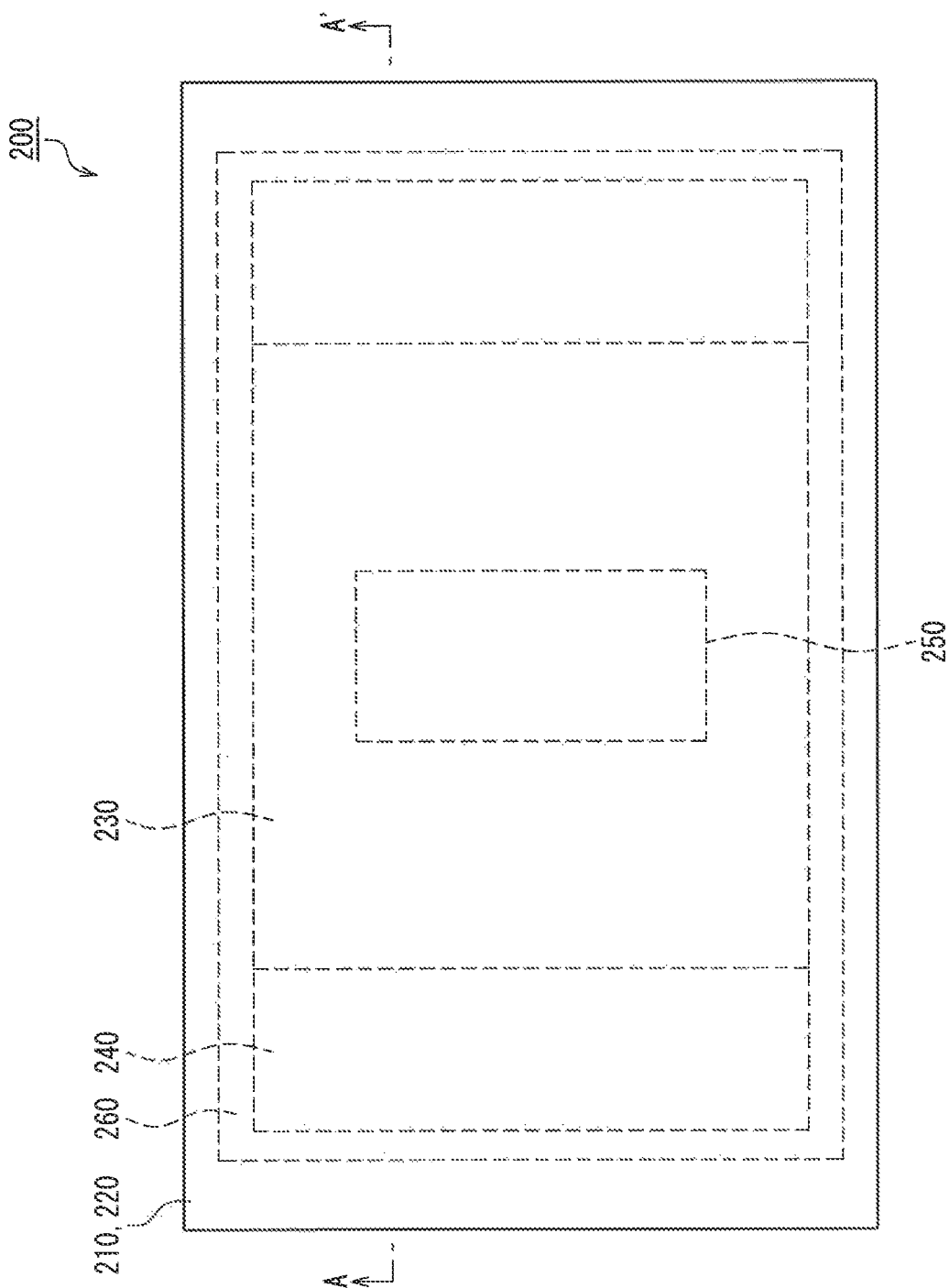
FIG. 5 is a plan view schematically illustrating an example of a waterproof device of Embodiment 2.

FIG. 5 is a diagram illustrating the wearable patch of Embodiment 2 when viewed from the outer surface side.

FIG. 4 shows a cross section taken along the line A-A in FIG. 5. In FIG. 4, the upper surface of the wearable patch 200 is referred to as an outer surface, and the lower surface of the wearable patch 200 is referred to as an inner surface. For the purpose of brevity, FIG. 5 shows only the positions of the main members in the wearable patch of this embodiment.

In the following description, the upper side and the lower side of FIG. 4 are appropriately referred to as an outer surface side and an inner surface side, respectively.

The following description is illustrative only, and the constituent members of the wearable patch of the present disclosure are not limited to the following description.

The wearable patch 200 of this embodiment may be, e.g., a medical patch for detecting the body temperature of the wearer and is used in direct contact with the skin.

As shown in FIG. 4, the wearable patch 200 of this embodiment includes a shell member 210 provided on the outer surface side, a shell member 220 provided on the inner surface side, an air cell, a drive circuit unit 240, a functional element 250, and an adhesive layer 260. The shell member 210 is composed of a water-repellent air-permeable sheet. The shell member 220 corresponds to a base. The air cell is a sheet-type cell in which a power generation element 230 is sealed between the shell member 210, which also serves as a sheet-type outer case member of the cell, and another sheet-type outer case member 235. The drive circuit unit 240 is provided on the inner surface of the sheet-type outer case member 235 of the air cell. The functional element 250 comes into contact with the skin of the wearer. The adhesive layer 260 is provided on the inner surface of the shell member 220 of the wearable patch 200 and located in a region other than the functional element 250. In the wearable patch 200 of this embodiment, the shell member 220 is formed in a region other than the portion where the functional element 250 is placed in contact with the drive circuit unit 240.

Each member of the power generation element 230, including a positive electrode 231 and a negative electrode 232, is in the form of a sheet. Accordingly, the air cell has a sheet shape with flexibility as a whole. In the wearable patch 200 of this embodiment, the shell member 210 is located near the positive electrode 231 of the air cell, and a portion of the shell member 210 that faces the positive electrode 231 is composed of a porous sheet with water repellency so that air (positive electrode active material) can be supplied to the positive electrode 231 when the wearable patch 200 is worn by the wearer.

Thus, the outer case member located on the positive electrode 231 side of the sheet-type cell can also be used as the shell member of the wearable patch 200. Therefore, the number of members can be reduced as compared to, e.g., the case where the sheet-type air cell is placed inside the shell member of the wearable patch. This can simplify the configuration of the entire device and can also reduce the size, weight, and cost of the device. Moreover, since the shell member 210 facing the positive electrode 231 of the air cell is composed of the water-repellent porous sheet, air can be stably supplied to the positive electrode 231 when the wearable patch 200 is worn by the wearer.

In the wearable patch 200 of this embodiment, the drive circuit unit 240 and the sheet-type air cell are stacked. This configuration can increase the ratio of the area of the air cell to the area of the wearable patch 200 and thus can increase the cell capacity.

Further, in the wearable patch 200 of this embodiment, the functional element 250 is a thin member made of a thin plate or a thin film, e.g., a sensor plate for detecting biological information of the wearer. As shown in FIG. 4, the functional element 250 with a small thickness may be stacked on the drive circuit unit 240.

When the drive circuit unit 240 and the functional element 250 are arranged in layers, the area of the drive circuit unit 240 can be increased with respect to the entire area of the wearable patch 200. This increases the design margin for the arrangement of various circuit components of the drive circuit unit 240. For example, the connection wiring may be shortened or thickened to reduce the resistance component, so that the drive circuit unit 240 can be operated with lower power consumption. Moreover, when the drive circuit unit 240 includes an antenna element, it is also possible to increase the area of the antenna element and to improve the antenna characteristics. Therefore, thinner circuit components can be selected, even though they have a relatively large area, to reduce the thickness of the drive circuit unit 240, which in turn reduces the thickness of the wearable patch 200 as a whole.

Since the functional element 250 and the drive circuit unit 240 are stacked, as shown in FIG. 5, the functional element 250 (sensor plate) can be located substantially in the central portion of the wearable patch 200 in a plan view. Thus, the adhesive layer 260 can be formed around the functional element 250, so that the wearable patch 200 can be firmly attached to the skin with the adhesive of the adhesive layer 260. Therefore, the functional element 250 (sensor plate) can be maintained in close contact with the skin of the wearer no matter how the wearer moves or sweats, or the contact portion of the wearable patch 200 gets wet with water.

The air cell, the drive circuit unit, the functional element, the exterior package serving as the shell member or the base, the configuration of the film members such as outer case members of the cell, and the material of the adhesive layer in the wearable patch 200 of Embodiment 2 are the same as those of Embodiment 1, and therefore the explanation will not be repeated.

EXAMPLES

Hereinafter, the present invention will be described in detail by way of examples of the waterproof device of the preset disclosure. However, the waterproof device of the present disclosure is not limited to the following examples.

Example 1

[Production of Sheet-Type Air Cell]
<Positive Electrode>
A composition for forming a catalyst-containing layer was prepared by mixing 30 parts by mass of carbon (Ketjenblack EC600JD manufactured by Lion Specialty Chemicals Co., Ltd.) with a DBP oil absorption of 495 $cm^3$/100 g and a specific surface area of 1270 $m^2$/g, 15 parts by mass of an acrylic dispersing agent, 60 parts by mass of SBR, and 500 parts by mass of water.

Using porous carbon paper (thickness: 0.25 mm, porosity: 75%, air permeability (Gurley): 70 sec/100 ml), the composition for forming a catalyst-containing layer was applied to the surface of the carbon paper by stripe coating so that the coating amount after drying was 10 mg/$cm^2$. Then, the composition was dried, resulting in a porous conductive base material that had a portion in which the catalyst-containing layer was formed and a portion in which no catalyst-containing layer was formed. This porous conductive base material was punched into a shape including a 15 mm×15 mm main body portion with the catalyst-containing layer and a 5 mm×15 mm terminal portion without the catalyst-containing layer. Thus, a positive electrode (air electrode) with a total thickness of 0.27 mm was produced.

<Negative Electrode>
Zinc alloy foil (thickness: 0.05 mm) containing additional elements of In: 0.05%, Bi: 0.04%, and Al: 0.001% was prepared. Then, the zinc alloy foil was punched into a shape including a 15 mm×15 mm main body portion and a 5 mm×15 mm terminal portion. Thus, a negative electrode with a theoretical capacity of about 65 mAh was produced.

<Electrolyte Solution>
An electrolyte solution was an ammonium sulfate aqueous solution with a concentration of 20% by mass (having a pH of 5.3, which was measured in an environment of 25° C. with a "LAQUA twin compact pH meter" manufactured by HORIBA, Ltd.).

<Separator>
A separator was produced by forming two graft films (each having a thickness of 15 μm) on both sides of a cellophane film (having a thickness of 20 μm). The graft films were composed of a graft copolymer obtained by graft copolymerization of acrylic acid with a polyethylene main chain. The total thickness of the separator was 50 μm.

<Water Repellent Membrane>
A water repellent membrane was a porous PTFE sheet with a thickness of 200 μm.

<Sheet-Type Package>
Two 25 mm×25 mm aluminum laminated films (thickness: 65 μm) were used to form a sheet-type package. Each of the aluminum laminated films had a structure in which a PET film was provided on the outer surface of aluminum foil, and a polypropylene film (heat-sealing resin layer) was provided on the inner surface of the aluminum foil.

Nine air holes, each having a diameter of 0.5 mm, were previously formed in one of the two aluminum laminated films. The air holes were spaced at regular intervals of 4.5 mm (length)×4.5 mm (width) (i.e., the center-to-center distance of adjacent air holes: 5 mm). Then, the water repellent membrane was thermally fused to the inner surface of this laminated film with a hot-melt adhesive. In the other aluminum laminated film, a modified polyolefin ionomer film was attached in parallel with the side of the laminated film to a portion where the terminal portions of the positive electrode and the negative electrode were to be arranged.

<Cell Assembly>
The aluminum laminated film having the water repellent membrane was put down, and then the positive electrode, the separator, and the negative electrode were formed in this order on the water repellent membrane. Moreover, the other aluminum laminated film was placed on top of them so that the modified polyolefin ionomer film was positioned on the terminal portions of the positive electrode and the negative electrode. Next, three sides of the two aluminum laminated films were thermally fused to each other, thus providing a bag-like outer case. After 0.1 ml of the electrolyte solution was injected through the opening of the bag-like outer case, the opening was sealed by thermal fusion, and consequently a sheet-type air cell was obtained. The thickness of the air cell (i.e., the length indicated by a in FIG. 3) was about 1.2 mm.

[Production of Waterproof Device]
A waterproof device was produced in the following manner using a measurement unit. The measurement unit included a drive circuit unit that was mounted on a flexible film substrate and included a memory, a processor, a transmitting and receiving circuit, and an antenna element. The measurement unit further included a functional element for measuring the body temperature of the wearer.

The sheet-type air cell was conductively connected to a connection terminal of the circuit unit. Then, the sheet-type air cell was placed on the circuit unit with the surface having the air holes facing away from the circuit unit. Thus, a stacked unit was formed. Although not shown, the position of the sheet-type air cell was adjusted so that the antenna element would not be covered with the aluminum laminated film of the sheet-type air cell, in order not to interfere with the communication function of the transmitting and receiving circuit.

Next, two water-repellent air-permeable sheets were prepared, each of which was a laminated sheet of a PE porous sheet and a PET nonwoven fabric sheet ("BREATHRON BRN3000E1" (trade name) manufactured by Nitoms, Inc., thickness: 0.25 mm, water pressure resistance: >80 kPa, air permeability: 400 sec/100 ml) and was cut to 50 mm×50 mm in size. An opening was provided in the central portion of one of the water-repellent air-permeable sheets so as to correspond to the size of the functional element of the stacked unit. Thus, a base was obtained.

Moreover, the film substrate of the stacked unit was bonded to the PE porous sheet of the base so that the functional element was exposed from the opening. Consequently, the stacked unit was integrated with the base.

The other water-repellent air-permeable sheet, which constituted an exterior package, was placed over the stacked unit with the PE porous sheet facing the sheet-type air cell. Then, the PE porous sheets at the periphery of the respective water-repellent air-permeable sheets were thermally fused to each other. Thus, a waterproof device was produced.

The waterproof device can be worn on the body by forming an adhesive layer on the lower surface of the base, as shown in FIG. 1, or by using a rubber band.

Example 2

A waterproof device was produced in the same manner as Example 1 except that each of the water-repellent air-permeable sheets was changed to a laminated sheet of a PE porous sheet and a nylon nonwoven fabric sheet ("BREATHRON BRN1860" (trade name) manufactured by Nitoms, Inc., thickness: 0.35 mm, water pressure resistance: >80 kPa, air permeability: 4500 sec/100 ml).

Example 3

A waterproof device was produced in the same manner as Example 1 except that each of the water-repellent air-permeable sheets was changed to a laminated sheet of a PE porous sheet and a PET nonwoven fabric sheet that differed from the laminated sheet used in Example 1 in air permeability ("BREATHRON BRN-A120E1" (trade name) manufactured by Nitoms, Inc., thickness: 0.25 mm, water pressure resistance: >80 kPa, air permeability: 28000 sec/100 ml).

Example 4

A waterproof device was produced in the same manner as Example 1 except that each of the water-repellent air-permeable sheets was changed to a PTFE porous sheet ("WP-020-80" manufactured by Sumitomo Electric Industries Ltd., thickness: 0.1 mm, water pressure resistance: 170 kPa, air permeability: 2500 sec/100 ml), and the peripheral portions of the respective water-repellent air-permeable sheets were thermally fused to each other after a PP sealing material had been sandwiched between them.

Example 5

A waterproof device was produced in the same manner as Example 1 except that each of the water-repellent air-permeable sheets was changed to a PE nonwoven fabric (thickness: 0.17 mm, water pressure resistance: 20 kPa, air permeability: 250 sec/100 ml), and the peripheral portions of the respective PE nonwoven fabrics were thermally fused to each other.

Comparative Example 1

A waterproof device was produced in the same manner as Example 1 except that each of the water-repellent air-permeable sheets was changed to a PE nonwoven fabric (thickness: 0.25 mm, water pressure resistance: 5 kPa, air permeability: 2 sec/100 ml), and the peripheral portions of the respective PE nonwoven fabrics were thermally fused to each other.

Comparative Example 2

A waterproof device was produced in the same manner as Example 1 except that each of the water-repellent air-permeable sheets was changed to a non-porous PP film without air permeability (thickness: 0.05 mm, water pressure resistance: >80 kPa, air permeability: >100000 sec/100 ml), and the peripheral portions of the respective PP films were thermally fused to each other.

The following evaluations were performed on the waterproof devices of Examples 1 to 5 and Comparative Examples 1 and 2.

(Water Immersion Test)

Each of the waterproof devices was immersed in water at a depth of 1 m for 30 minutes in accordance with the method defined in JIS C 0920. After the waterproof device was taken out of the water, the exterior package was cut open to visually check whether or not water entered the inside of the device. Thus, the waterproofness of each of the waterproof devices was evaluated.

(Check of Operation of Air Cell)

After assembly, each of the waterproof devices was allowed to stand still in a room with a relative humidity of 60% at 35° C., and the time it took until the information sent from the device could not be received was measured. Then, the operating time of the air cell under dry conditions was confirmed.

Next, after assembly, each of the waterproof devices (which were different from those used to measure the operating time of the air cell under dry conditions) was immersed in water at a depth of 1 m for 30 minutes. After the waterproof device was taken out of the water, it was allowed to stand still in a room with a relative humidity of 60% at 35° C., and the time it took until the information sent from the device could not be received was measured. Then, the operating time of the air cell under wet conditions was confirmed.

Table 1 shows the configurations of the water-repellent air-permeable sheets used for the exterior packages of the waterproof devices of the examples and the comparative examples. Table 2 shows the evaluation results when the operating time of the air cell under dry conditions of the waterproof device of Example 1 was set to 100.

TABLE 1

| | Water-repellent air-permeable sheet | | | |
| --- | --- | --- | --- | --- |
| | Configuration | Thickness (mm) | Water pressure resistance (kPa) | Air permeability (sec/100 ml) |
| Example 1 | PE porous sheet/PET nonwoven fabric sheet | 0.25 | >80 | 400 |
| Example 2 | PE porous sheet/nylon nonwoven fabric sheet | 0.35 | >80 | 4500 |
| Example 3 | PE porous sheet/PET nonwoven fabric sheet | 0.25 | >80 | 28000 |
| Example 4 | PTFE porous sheet | 0.1 | 170 | 2500 |
| Example 5 | PE nonwoven fabric | 0.17 | 20 | 250 |
| Comparative Example 1 | PE nonwoven fabric | 0.25 | 5 | 2 |

TABLE 1-continued

| | Water-repellent air-permeable sheet | | | |
|---|---|---|---|---|
| | Configuration | Thickness (mm) | Water pressure resistance (kPa) | Air permeability (sec/100 ml) |
| Comparative Example 2 | PP film (non-porous) | 0.05 | >80 | >100000 |

TABLE 2

| | Waterproofness (presence or absence of water penetration) | Operating time of air cell | |
|---|---|---|---|
| | | Dry conditions | Wet conditions |
| Example 1 | absence | 100 | 100 |
| Example 2 | absence | 100 | 100 |
| Example 3 | absence | 100 | 100 |
| Example 4 | absence | 100 | 100 |
| Example 5 | absence | 100 | 100 |
| Comparative Example 1 | presence | 100 | 0 |
| Comparative Example 2 | absence | 0.3 | 0.3 |

As shown in Tables 1 and 2, in the waterproof devices of Examples 1 to 5, the sheet-type air cell was able to be operated and the function of the air cell was well maintained even after the immersion of the waterproof device in water, since the circuit unit and the cell were protected by the exterior package composed of the water-repellent air-permeable sheet with an appropriate water pressure resistance.

On the other hand, in the waterproof device of Comparative Example 1 having the exterior package composed of the sheet with an excessively low water pressure resistance, water entered the inside of the device during the immersion in water due to insufficient waterproofness, and thus the water blocked the flow path of air and prevented the air from being supplied to the positive electrode of the sheet-type air cell. As a result, the device was unable to be operated. In the waterproof device of Comparative Example 2 having the exterior package composed of the non-porous PP film, although the waterproofness was good, the flow of air into the device was obstructed by the exterior package, and thus the sheet-type air cell was not substantially discharged. As a result, the device was unable to be operated regardless of the conditions.

(Characteristic Evaluation of Wearable Patch of Embodiment 2)

Next, in the wearable patch of Embodiment 2, the discharge capacities of the air cells with different electrolyte solutions were measured and compared. The results will be described below.

In each of the sheet-type air cells, the positive electrode, the negative electrode, the electrolyte solution, the separator, the water repellent membrane, and the outer case members were made of the following materials.

<Positive Electrode>

A composition for forming a catalyst layer was prepared by mixing 30 parts by mass of carbon (Ketjenblack EC600JD (trade name) manufactured by Lion Specialty Chemicals Co., Ltd.) with a DBP oil absorption of 495 cm$^3$/100 g and a specific surface area of 1270 m$^2$/g, 15 parts by mass of an acrylic dispersing agent, 60 parts by mass of SBR, and 500 parts by mass of water.

Using a porous carbon sheet (thickness: 0.25 mm, porosity: 75%, air permeability (Gurley): 70 sec/100 ml), the composition for forming a catalyst layer was applied to the surface of the carbon sheet by stripe coating so that the coating amount after drying was 10 mg/cm$^2$. Then, the composition was dried, resulting in a current collector that had a portion in which the catalyst layer was formed and a portion in which no catalyst layer was formed. This current collector was punched into a shape including the portion with the catalyst layer that was 15 mm×15 mm in size and the portion without the catalyst layer that was 5 mm×15 mm in size. The portion without the catalyst layer was located at one end of the 15 mm×15 mm portion and was to be a lead. Thus, a positive electrode (air electrode) with a total thickness of 0.27 mm was produced.

<Negative Electrode>

Zinc alloy foil (thickness: 0.05 mm) containing additional elements of In: 0.05%, Bi: 0.04%, and Al: 0.001% was prepared. Then, the zinc alloy foil was punched into a shape including a portion that was 15 mm×15 mm in size and served as an active material, and a portion that was 5 mm×15 mm in size, was located at one end of the 15 mm×15 mm portion, and was to be a lead. Thus, a negative electrode was produced.

<Electrolyte Solution>

Cell 1: 20% by mass of ammonium sulfate aqueous solution (pH=5.3)

Cell 2: 20% by mass of ammonium chloride aqueous solution (pH=4.3)

Cell 3: 20% by mass of sodium chloride aqueous solution (pH=7)

Cell 4: 30% by mass of potassium hydroxide aqueous solution (pH=14)

<Separator>

A separator was produced by forming two graft films (each having a thickness of 15 μm) on both sides of a cellophane film (having a thickness of 20 μm). The graft films were composed of a graft copolymer obtained by graft copolymerization of acrylic acid with a polyethylene main chain.

<Water Repellent Membrane>

A water repellent membrane was a PTFE sheet with a thickness of 200 μm.

<Outer Case Member>

A 2.5 cm×5 cm aluminum laminated film that was an outer case member located on the positive electrode side and constituted a shell member, and a 2.5 cm×2.5 cm aluminum laminated film that was an outer case member located on the negative electrode side were used. Each of the aluminum laminated films had a structure in which a PET film was provided on the outer surface of aluminum foil, and a polypropylene film (heat-sealing resin layer) was provided on the inner surface of the aluminum foil.

<Cell Assembly>

Nine air holes, each having a diameter of 0.5 mm, were formed in the laminated film that was located on the positive electrode side to constitute the shell member. The air holes corresponded to the position of the catalyst layer of the positive electrode. The air holes were arranged in a matrix and spaced at regular intervals of 4.5 mm (length)×4.5 mm (width) (i.e., the center-to-center distance of adjacent air holes: 5 mm). Then, the water repellent membrane was thermally fused to the inner surface of this laminated film with a hot-melt adhesive. In the laminated film that was the outer case member located on the negative electrode side, a modified polyolefin ionomer film was attached in parallel with the side of the laminated film to a portion where the leads of the positive electrode and the negative electrode were to be arranged, in order to improve the sealing properties of the thermally fused portion between the leads and the outer case member.

The laminated film constituting the shell member was put down, and then the positive electrode, the separator, and the negative electrode were formed in this order on the water repellent membrane. Moreover, the laminated film that was the outer case member located on the negative electrode side was placed on top of them so that the modified polyolefin ionomer film was positioned on the leads of the positive electrode and the negative electrode. Next, three sides of the laminated film that was the outer case member located on the negative electrode side were thermally fused to the opposing laminated film, thus providing a bag-like outer case. After the electrolyte solution was injected through the opening of the bag-like outer case, the opening was sealed by thermal fusion, and consequently a sheet-type air cell was obtained. The thickness of the air cell was about 1 mm.

Each of the air cells thus obtained was allowed to stand in the atmosphere for 10 minutes, and then discharged to 0.5 V at a current corresponding to the 100 hour rate with respect to the design capacity of the cell. At this time, the discharge capacity of the cell was measured. Table 3 shows the results.

TABLE 3

|        | Discharge capacity (mAh) |
|--------|--------------------------|
| Cell 1 | 35                       |
| Cell 2 | 33                       |
| Cell 3 | 30                       |
| Cell 4 | 36                       |

Compared to the air cell (cell 4) including a high concentration alkaline electrolyte solution, which is used as an electrolyte solution of a commercially available button-type air cell, the air cells (cells 1 to 3) including the electrolyte solution that is much safer than the alkaline electrolyte solution can achieve sufficient discharge capacity. In particular, the cells 1 and 2, in which the salts of strong acids and weak bases are used as electrolyte salts, can have excellent properties that are substantially the same as those of the cell 4 including the electrolyte solution similar to that of the commercially available button-type air cell.

The above results confirm that the air cell of this embodiment has a small thickness, good handleability, and high safety. Moreover, the air cell has a relatively large capacity and is suitable as a power source for the device that is worn directly on the body.

When the above cell is stacked on, e.g., the drive circuit unit or the shell member of 2.5 cm×5 cm provided on the inner surface side, as will be described later, the wearable patch can be configured such that the outer case member of the cell constitutes the shell member provided on the outer surface side of the entire device.

As described above, in the waterproof device of the present disclosure, at least a part of the exterior package is composed of the water-repellent air-permeable sheet with a water pressure resistance of 12 kPa or more. Thus, the waterproof device can use, as an operating power source contained in the exterior package, the air cell that requires air (oxygen) as a positive electrode active material.

In the wearable patch (waterproof device) of the present disclosure, the shell member provided on the outer surface side, which forms the main body of the patch, also serves as the outer case member that is on the outer side of the air cell (operating power source). The air cell is inserted between the shell member provided on the outer surface side and the opposing shell member provided on the inner surface side of the wearable patch. Therefore, the number of constituent members can be reduced as compared to the case where the air cell is placed inside the shell member of the wearable patch. Moreover, in the air cell that uses air as a positive electrode active material, the surface of the positive electrode needs to communicate with the outside of the wearable patch. In this embodiment, since the shell member of the wearable patch also serves as the outer case member located on the positive electrode side of the air cell, it is only necessary that a portion of the shell member that faces the positive electrode be composed of the water-repellent air-permeable sheet. This can further simplify the production process of the wearable patch and reduce the cost, as compared to a configuration in which both the outer case member of the air cell and the shell member of the wearable patch that are located on the positive electrode side should have, e.g., openings to allow air to pass through them.

The outer case of the air cell may be made of a resin film on which a metal thin film such as aluminum foil is formed. This can reliably prevent leakage of the electrolyte solution contained in the outer case of the air cell. However, when the laminated material of the resin film and the metal thin film forms the entire shell member provided on the outer surface side, the antenna element of the drive circuit unit may be shielded to interfere with the communication between the drive circuit unit and the external device.

Therefore, it is preferable that the shape and arrangement of the shell member and the lead are adjusted so that the antenna element will not be covered with metal components such as the metal thin film of the shell member provided on the outer surface side, in order not to interfere with the communication with the outside.

For example, the antenna element may be located away from the other circuit components of the drive circuit unit or may be exposed by making a notch in the shell member so that radio waves are not shielded. Moreover, when infrared communication is used as a communication means between the drive circuit unit and the external device, a part of the shell member provided on the outer surface side may be made transparent to allow infrared light to pass through it.

In the above embodiments, the air cell includes the electrolyte solution in the liquid state. When a gel electrolyte is used, the material of the outer case of the air cell may be a resin film on which no metal foil is formed. In this case, the air cell can be produced by printing, and thus the production process of the wearable patch can be further simplified.

In the above embodiments, a portion of the shell member that faces a region in which the positive electrode is formed is composed of a porous sheet with water repellency. It is preferable that a portion of the shell member that faces at least the region in which the positive electrode is formed is composed of a resin nonwoven fabric.

The sheet-type cell (operating power source) is not limited to the air cell and may be a known sheet-type cell such as a manganese cell as long as the cell capacity is consistent with the intended use of the wearable patch. In this case, there is no need to use the laminated material including metal foil to form the shell member provided on the outer surface side of the wearable patch or the outer case of the sheet-type cell. Moreover, unlike the air cell, the positive electrode does not have to be on the outer surface side.

In the above embodiments, the shell member is provided on the inner surface side of the wearable patch. Since the drive circuit unit may be formed as a resin sheet, the shell member provided on the inner surface side is not an essential component of the wearable patch. When the shell member is not provided on the inner surface side of the wearable patch, the adhesive layer is directly formed on the inner surface of the drive circuit unit (resin sheet) and on the inner surface of the shell member provided on the outer surface side.

In the above embodiments, the drive circuit unit is placed in a region corresponding to the power generation element of the air cell, and the functional element is stacked on the drive circuit unit. That is, as shown in FIG. 5, the positions of the power generation element of the air cell, the drive circuit unit, and the functional element overlap with each other when the wearable patch is seen in a plan view. However, in the waterproof device or wearable patch of the present disclosure, it is not essential that all the air cell, the drive circuit unit, and the functional element are stacked on top of each other.

For example, as described above, the means for communicating with the external device such as the antenna element of the drive circuit unit may be displaced from the power generation element of the air cell in the principal surface direction of the wearable patch.

In the above embodiments, the thin-film sensor plate is used as an example of the functional element to detect, e.g., the body temperature and heart rate of the wearer. The wearable patch of the present disclosure may be a medical device including a functional element that has the function of administering a drug solution to the wearer by injection. When the functional element has the administration function, it requires a tank for containing the drug solution and a mechanism for delivering a predetermined amount of the drug solution with predetermined timing. Therefore, the thickness of the functional element is increased. In such a case, the position of the functional element may be displaced from the position of at least one of the air cell and the drive circuit unit in the principal surface direction of the wearable patch, thus avoiding an increase in the thickness of the wearable patch. Even if the area of the wearable patch becomes large, this configuration allows the wearer to wear the wearable patch without feeling uncomfortable.

[Supplementary Provided Items]

In Embodiment 2 of the present disclosure, the waterproof device has a configuration in which the outer case member located on the positive electrode side of the air cell constitutes the exterior package of the entire device, and the exterior package of the entire device is composed of the water-repellent air-permeable sheet.

The configuration in which the outer case member of the sheet-type air cell constitutes the exterior package (shell member) of the device, as described with the wearable patch of Embodiment 2, can be applied to various devices that are different from the wearable patch including the air cell, the drive circuit unit, and the functional element and use a sheet material other than the water-repellent air-permeable sheet to form the exterior package of the entire device.

In this case, the exterior package (shell member) of the entire device may be composed of, e.g., a resin sheet (made of PE, PP polyethylene terephthalate, nylon, etc.). Moreover, the exterior package (which serves as both the shell member of the device such as a wearable patch and the outer case member of the air cell) has air holes in at least a portion facing the positive electrode of the air cell so as to supply air. Thus, the positive electrode communicates with the outside of the wearable patch.

For example, if the wearable patch of Embodiment 2 does not need to be waterproof, the configuration may be identical to that described in Embodiment 2 except for the exterior package provided on the outer surface side.

Supplementary items regarding the configuration of a wearable patch other than the waterproof device will be described below. The following device (wearable patch) includes a functional element that comes into contact with the skin, a drive circuit unit that operates the functional element, a sheet-type cell in which a power generation element, including a positive electrode and a negative electrode, is sealed between two sheet-type outer case members, and an adhesive layer that is formed on the inner surface. One of the sheet-type outer case members that is on the outer side of the sheet-type cell constitutes a part of the exterior package that is a shell member provided on the outer surface side of the entire device. Thus, the device can have a simple configuration with a reduced number of members constituting the device, as compared to a configuration in which the cell (operating power source) and the drive circuit unit are placed inside the shell member, i.e., the exterior package that forms a shell of the device.

Consequently, the above device can be compact and lightweight while using the sheet-type cell with necessary capacity to perform the function, and is not likely to give an uncomfortable feeling to the wearer.

[Supplementary Item 1]

A wearable patch that is worn directly on the body, comprising:

a functional element that comes into contact with skin;

a drive circuit unit that operates the functional element;

a sheet-type cell in which a power generation element, including a positive electrode and a negative electrode, is sealed between two sheet-type outer case members; and an adhesive layer that is formed on an inner surface, wherein one of the sheet-type outer case members that is on an outer side of the sheet-type cell constitutes a part of a shell member provided on an outer surface side of the entire device.

[Supplementary Item 2]

The wearable patch according to supplementary item 2, wherein the drive circuit unit and the sheet-type cell are stacked.

[Supplementary Item 3]

The wearable patch according to supplementary item 1 or 2, wherein the cell is an air cell, and the sheet-type outer case member that is on the outer side of the sheet-type cell has air holes in a portion facing the positive electrode.

INDUSTRIAL APPLICABILITY

As described above, the waterproof device of the present disclosure is a wearable device and includes a circuit unit, a power source, and an exterior package that protects the circuit unit and the power source. At least a part of the exterior package is composed of a water-repellent air-permeable sheet. The water-repellent air-permeable sheet has a water pressure resistance of 12 kPa or more. With this configuration, the waterproof device of the present disclosure can be designed for a situation where it is used in water. Moreover, the waterproof device can also use an air cell with a large cell capacity as an operating power source, and thus can achieve a long-term operation.

Therefore, the present disclosure is useful as a waterproof device for various purposes, mainly in the medical field including the measurement of physical data of the wearer and the injection of a drug solution.

DESCRIPTION OF REFERENCE NUMERALS

1 Power source (cell)
10 Sheet-type air cell
20 Positive electrode (air electrode)
20a Positive electrode terminal
30 Negative electrode
30a Negative electrode terminal
40 Separator
50 Water repellent membrane
60 Sheet-type package (sheet-type outer case)
61 Air hole
100 Waterproof device
110 Drive circuit unit (circuit unit)
120 Exterior package
121 Water-repellent air-permeable sheet
122 Base
130 Adhesive layer
140 Functional element (circuit unit)
200 Wearable patch
210 Shell member (on outer surface side: outer case member on positive electrode side)
220 Shell member on inner surface side
230 Power generation element
231 Positive electrode
232 Negative electrode
235 Outer case member on negative electrode side
240 Drive circuit unit
250 Sensor plate (functional element)
260 Adhesive layer

The invention claimed is:

1. A waterproof device that is worn on the body, comprising:
a circuit unit;
a power source; and
an exterior package that protects the circuit unit and the power source,
wherein the power source is a sheet-type air cell, and an electrolyte of the sheet-type air cell is an aqueous solution that contains an electrolyte salt and has a pH of 3 or more and less than 12,
an adhesive layer is provided on an inner surface of the device,
at least a part of the exterior package is composed of a water-repellent air-permeable sheet, and
the water-repellent air-permeable sheet has a water pressure resistance of 12 kPa or more.

2. The waterproof device according to claim 1, wherein the water-repellent air-permeable sheet has an air permeability of 60000 sec/100 ml or less.

3. The waterproof device according to claim 1, wherein the water-repellent air-permeable sheet has a thickness of 0.01 to 3 mm.

4. The waterproof device according to claim 1, wherein the water-repellent air-permeable sheet is a laminated sheet of a porous sheet with water repellency and a support sheet, and
the support sheet is a nonwoven fabric sheet or a rubber sheet.

5. The waterproof device according to claim 4, wherein the porous sheet is made of polyethylene, polypropylene, or polytetrafluoroethylene.

6. The waterproof device according to claim 4, wherein the nonwoven fabric sheet is made of polyethylene, polypropylene, polytetrafluoroethylene, or nylon.

7. The waterproof device according to claim 4, wherein the rubber sheet is a urethane rubber sheet or a silicone rubber sheet.

8. The waterproof device according to claim 1, comprising:
a functional element that comes into contact with the skin;
a drive circuit unit that operates the functional element; and
a sheet-type cell as the power source in which a power generation element, including a positive electrode and a negative electrode, is sealed between two sheet-type outer case members,
wherein one of the sheet-type outer case members that is on an outer side of the sheet-type cell constitutes a part of the exterior package that is a shell member provided on an outer surface side of the entire device.

9. The waterproof device according to claim 8, wherein the drive circuit unit and the sheet-type cell are stacked.

10. The waterproof device according to claim 8, wherein the cell is an air cell, and the water-repellent air-permeable sheet is disposed in a portion of the sheet-type outer case member that is on the outer side of the sheet-type cell and faces the positive electrode.

11. The waterproof device according to claim 1, wherein the water-repellent air-permeable sheet is disposed in a portion of the exterior package that faces a positive electrode of the sheet-type air cell.

* * * * *